United States Patent
Bowman et al.

(10) Patent No.: US 9,579,188 B2
(45) Date of Patent: Feb. 28, 2017

(54) ANCHOR HAVING A CONTROLLED DRIVER ORIENTATION

(71) Applicant: SMITH & NEPHEW, INC., Memphis, TN (US)

(72) Inventors: Steve Mark Bowman, Sherborn, MA (US); Alfred R. Berube, North Attleboro, MA (US); Bernard Joseph Bourque, Rehoboth, MA (US); Wei Yang, Lexington, MA (US); Mark Edwin Housman, North Attleborough, MA (US); John Stroncek, Boston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 581 days.

(21) Appl. No.: 14/085,295

(22) Filed: Nov. 20, 2013

(65) Prior Publication Data

US 2014/0081339 A1 Mar. 20, 2014

Related U.S. Application Data

(63) Continuation-in-part of application No. 13/044,777, filed on Mar. 10, 2011, now Pat. No. 8,979,865.
(Continued)

(51) Int. Cl.
*A61B 17/86* (2006.01)
*A61F 2/08* (2006.01)
(Continued)

(52) U.S. Cl.
CPC ........ *A61F 2/0811* (2013.01); *A61B 17/0401* (2013.01); *A61B 17/869* (2013.01);
(Continued)

(58) Field of Classification Search
CPC .............. A61B 17/8645; A61B 17/864; A61B 17/8875; B25B 13/59
(Continued)

(56) References Cited

U.S. PATENT DOCUMENTS

| 2,288,864 A | * | 7/1942 | Whitehead | ............ B25B 31/005 411/436 |
| 3,320,783 A | * | 5/1967 | Kerr | ........................ E05B 19/18 70/395 |

(Continued)

FOREIGN PATENT DOCUMENTS

| CN | 1701775 A | 11/2005 |
| CN | 1829479 A | 9/2006 |

(Continued)

OTHER PUBLICATIONS

Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.
(Continued)

*Primary Examiner* — Nicholas Woodall
(74) *Attorney, Agent, or Firm* — Burns & Levinson LLP; Joseph M. Maraia

(57) ABSTRACT

The present disclosure relates to an interference screw having a body with a proximal end, distal end, and longitudinal axis extending between thereinbetween. The screw further includes threads for fixing the screw into bone. The screw further includes a through bore defined by the body. The through bore extends between the proximal and distal ends along the longitudinal axis, and has a surface. The screw further includes a controlling member formed by the through bore surface. To install the screw into bone, a surgeon turns the screw with a driver that engages with the controlling member. The driver only engages the controlling
(Continued)

member when it is in a driving orientation with respect to the controlling member. Advantageously, with this "one-way" engagement the surgeon can control and confirm the orientation of the driver without seeing the driver and/or screw.

8 Claims, 19 Drawing Sheets

Related U.S. Application Data

(60) Provisional application No. 61/312,291, filed on Mar. 10, 2010, provisional application No. 61/334,808, filed on May 14, 2010, provisional application No. 61/359,080, filed on Jun. 28, 2010.

(51) Int. Cl.
*A61B 17/04* (2006.01)
*A61B 17/88* (2006.01)
*A61B 17/00* (2006.01)

(52) U.S. Cl.
CPC ........ *A61B 17/8645* (2013.01); *A61B 17/888* (2013.01); *A61B 17/8888* (2013.01); *A61F 2/0805* (2013.01); *A61B 17/864* (2013.01); *A61B 2017/00455* (2013.01); *A61B 2017/00477* (2013.01); *A61B 2017/00964* (2013.01); *A61B 2017/044* (2013.01); *A61B 2017/0409* (2013.01); *A61B 2017/0458* (2013.01); *A61F 2002/0841* (2013.01); *A61F 2002/0858* (2013.01); *A61F 2002/0888* (2013.01); *A61F 2250/0097* (2013.01)

(58) Field of Classification Search
USPC .............................. 81/124.6, 443, 459–461
See application file for complete search history.

(56) References Cited

U.S. PATENT DOCUMENTS

| | | | |
|---|---|---|---|
| 3,499,222 A | 3/1970 | Linkow et al. | |
| 3,716,058 A | 2/1973 | Tanner | |
| 3,821,975 A * | 7/1974 | Haker ................... | B25B 13/485 411/427 |
| 3,869,942 A | 3/1975 | DeCaro | |
| 3,874,258 A * | 4/1975 | Semola ................. | B25B 13/485 411/427 |
| 4,027,572 A * | 6/1977 | Burge ................... | B25B 13/485 411/436 |
| 4,177,797 A | 12/1979 | Baylis et al. | |
| D288,777 S * | 3/1987 | Kwon ............................ | D8/397 |
| 4,653,489 A | 3/1987 | Tronzo | |
| 4,738,255 A | 4/1988 | Goble et al. | |
| 4,741,651 A | 5/1988 | Despres | |
| 4,834,757 A | 5/1989 | Brantigan | |
| 4,854,311 A | 8/1989 | Steffee | |
| RE33,114 E * | 11/1989 | Chiavon ............... | B25B 13/485 411/429 |
| 4,913,143 A | 4/1990 | Oloff et al. | |
| 4,961,740 A | 10/1990 | Ray et al. | |
| 4,988,351 A | 1/1991 | Paulos et al. | |
| 5,026,373 A | 6/1991 | Ray et al. | |
| 5,055,104 A | 10/1991 | Ray | |
| 5,116,337 A | 5/1992 | Johnson | |
| 5,129,904 A | 7/1992 | Illi | |
| 5,129,906 A | 7/1992 | Ross et al. | |
| 5,139,520 A | 8/1992 | Rosenberg | |
| 5,197,967 A | 3/1993 | Wilson | |
| 5,236,431 A | 8/1993 | Gogolewski et al. | |
| 5,242,447 A | 9/1993 | Borzone | |
| 5,354,299 A | 10/1994 | Coleman | |
| 5,364,400 A | 11/1994 | Rego, Jr. et al. | |
| 5,370,662 A | 12/1994 | Stone et al. | |
| 5,383,878 A | 1/1995 | Roger et al. | |
| 5,407,427 A | 4/1995 | Zhu et al. | |
| 5,411,506 A | 5/1995 | Goble et al. | |
| 5,411,523 A | 5/1995 | Goble | |
| 5,423,823 A | 6/1995 | Schmieding | |
| 5,447,533 A | 9/1995 | Vachon et al. | |
| 5,464,427 A | 11/1995 | Curtis et al. | |
| 5,470,334 A | 11/1995 | Ross et al. | |
| 5,531,780 A | 7/1996 | Vachon | |
| 5,571,139 A | 11/1996 | Jenkins, Jr. | |
| 5,573,548 A | 11/1996 | Nazre et al. | |
| 5,593,409 A | 1/1997 | Michelson | |
| 5,609,635 A | 3/1997 | Michelson | |
| 5,626,613 A | 5/1997 | Schmieding | |
| 5,632,747 A | 5/1997 | Scarborough | |
| 5,645,547 A | 7/1997 | Coleman | |
| 5,658,285 A | 8/1997 | Marnay et al. | |
| 5,676,545 A | 10/1997 | Jones | |
| 5,681,352 A | 10/1997 | Clancy, III et al. | |
| 5,690,676 A | 11/1997 | Dipoto et al. | |
| 5,695,497 A | 12/1997 | Stahelin | |
| 5,702,397 A | 12/1997 | Goble et al. | |
| 5,709,683 A | 1/1998 | Bagby | |
| 5,802,794 A | 9/1998 | Robson | |
| 5,833,715 A | 11/1998 | Vachon et al. | |
| 5,876,405 A | 3/1999 | Del Rio | |
| 5,888,227 A | 3/1999 | Cottle | |
| 5,891,146 A | 4/1999 | Simon et al. | |
| 5,921,982 A | 7/1999 | Lesh et al. | |
| 5,951,560 A | 9/1999 | Simon et al. | |
| 5,961,524 A | 10/1999 | Crombie | |
| 5,964,783 A | 10/1999 | Grafton et al. | |
| 5,968,047 A | 10/1999 | Reed | |
| 5,968,098 A | 10/1999 | Winslow | |
| 5,984,967 A | 11/1999 | Zdeblick et al. | |
| 6,008,433 A | 12/1999 | Stone | |
| 6,039,762 A | 3/2000 | McKay | |
| 6,086,593 A | 7/2000 | Bonutti | |
| 6,096,060 A | 8/2000 | Fitts et al. | |
| 6,097,986 A | 8/2000 | Janke et al. | |
| 6,196,780 B1 | 3/2001 | Wakai et al. | |
| 6,214,031 B1 | 4/2001 | Schmieding et al. | |
| 6,235,057 B1 | 5/2001 | Roger et al. | |
| 6,283,973 B1 | 9/2001 | Hubbard et al. | |
| 6,302,632 B1 * | 10/2001 | Lin ....................... | B25B 15/005 411/404 |
| 6,360,129 B1 | 3/2002 | Ley et al. | |
| 6,443,989 B1 | 9/2002 | Jackson | |
| 6,447,545 B1 | 9/2002 | Bagby | |
| 6,488,683 B2 | 12/2002 | Lieberman | |
| 6,511,499 B2 | 1/2003 | Schmieding et al. | |
| 6,514,257 B2 | 2/2003 | Dovesi et al. | |
| 6,517,542 B1 | 2/2003 | Papay et al. | |
| 6,527,774 B2 | 3/2003 | Lieberman | |
| 6,544,265 B2 | 4/2003 | Lieberman | |
| 6,551,319 B2 | 4/2003 | Lieberman | |
| 6,551,320 B2 | 4/2003 | Lieberman | |
| 6,551,322 B1 | 4/2003 | Lieberman | |
| 6,554,830 B1 | 4/2003 | Chappius | |
| 6,589,245 B1 | 7/2003 | Weiler et al. | |
| 6,604,945 B1 | 8/2003 | Jones | |
| 6,626,917 B1 | 9/2003 | Craig | |
| 6,648,903 B1 | 11/2003 | Pierson | |
| 6,656,183 B2 | 12/2003 | Colleran et al. | |
| 6,823,871 B2 | 11/2004 | Schmieding | |
| 6,855,168 B2 | 2/2005 | Crozet | |
| 6,863,671 B1 | 3/2005 | Strobel et al. | |
| 6,942,669 B2 | 9/2005 | Kurc | |
| 6,953,462 B2 | 10/2005 | Lieberman | |
| 7,033,372 B1 | 4/2006 | Cahalan | |
| 7,070,586 B2 | 7/2006 | Hart et al. | |
| 7,083,647 B1 | 8/2006 | Sklar et al. | |
| 7,090,690 B2 | 8/2006 | Foerster et al. | |
| 7,189,251 B2 | 3/2007 | Kay | |
| 7,195,634 B2 | 3/2007 | Schmieding et al. | |
| 7,217,279 B2 | 5/2007 | Reese | |
| 7,322,978 B2 | 1/2008 | West | |
| 7,322,986 B2 | 1/2008 | Wolf | |
| 7,594,929 B2 | 9/2009 | Collette | |

(56) References Cited

U.S. PATENT DOCUMENTS

| | | |
|---|---|---|
| 7,608,098 B1 | 10/2009 | Stone et al. |
| 7,867,252 B2 | 1/2011 | Criscuolo et al. |
| 7,914,539 B2 | 3/2011 | Stone et al. |
| 8,016,865 B2 | 9/2011 | Donnelly et al. |
| 8,034,090 B2 | 10/2011 | Stone et al. |
| 8,343,186 B2 | 1/2013 | Dreyfuss et al. |
| 8,623,052 B2 | 1/2014 | Dreyfuss et al. |
| 8,636,799 B2 | 1/2014 | Sklar et al. |
| 8,672,967 B2 | 3/2014 | DiMatteo et al. |
| 8,801,755 B2 | 8/2014 | Dreyfuss et al. |
| 8,821,541 B2 | 9/2014 | Dreyfuss et al. |
| 2002/0022862 A1 | 2/2002 | Grafton et al. |
| 2002/0052629 A1 | 5/2002 | Morgan et al. |
| 2002/0055737 A1 | 5/2002 | Lieberman |
| 2002/0055738 A1 | 5/2002 | Lieberman |
| 2002/0055742 A1 | 5/2002 | Lieberman |
| 2002/0087189 A1 | 7/2002 | Bonutti |
| 2002/0087190 A1 | 7/2002 | Benavitz et al. |
| 2002/0099382 A1 | 7/2002 | Salazar et al. |
| 2002/0111653 A1 | 8/2002 | Foerster |
| 2002/0143335 A1 | 10/2002 | von Hoffmann et al. |
| 2002/0165546 A1 | 11/2002 | Goble et al. |
| 2003/0055431 A1 | 3/2003 | Brannon |
| 2003/0065361 A1 | 4/2003 | Dreyfuss |
| 2003/0065374 A1 | 4/2003 | Honeck |
| 2003/0069640 A1 | 4/2003 | Ferreira et al. |
| 2003/0125749 A1 | 7/2003 | Yuan et al. |
| 2003/0181913 A1 | 9/2003 | Lieberman |
| 2003/0195529 A1 | 10/2003 | Takamoto et al. |
| 2004/0015170 A1 | 1/2004 | Tallarida et al. |
| 2004/0030343 A1 | 2/2004 | Kurc |
| 2004/0039404 A1 | 2/2004 | Dreyfuss |
| 2004/0073216 A1 | 4/2004 | Lieberman |
| 2004/0097945 A1 | 5/2004 | Wolf |
| 2004/0122424 A1 | 6/2004 | Ferree |
| 2004/0143158 A1 | 7/2004 | Hart et al. |
| 2004/0143237 A1 | 7/2004 | Hart et al. |
| 2004/0153074 A1 | 8/2004 | Bojarski et al. |
| 2004/0267265 A1 | 12/2004 | Kyle |
| 2005/0107828 A1 | 5/2005 | Reese |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1 | 12/2005 | Corradi et al. |
| 2005/0283239 A1 | 12/2005 | Crozet |
| 2006/0009769 A1 | 1/2006 | Lieberman |
| 2006/0030948 A1 | 2/2006 | Manrique et al. |
| 2006/0079895 A1 | 4/2006 | McLeer |
| 2006/0100627 A1 | 5/2006 | Stone et al. |
| 2006/0106390 A1 | 5/2006 | Jensen et al. |
| 2006/0142769 A1 | 6/2006 | Collette |
| 2006/0149266 A1 | 7/2006 | Cordasco |
| 2006/0217681 A1 | 9/2006 | Hart et al. |
| 2006/0241636 A1 | 10/2006 | Novak et al. |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0032797 A1 | 2/2007 | Ortiz et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0248029 A1 | 10/2009 | Paulos |
| 2009/0319043 A1 | 12/2009 | McDevitt et al. |
| 2010/0106166 A1 | 4/2010 | Cropper et al. |
| 2011/0112576 A1 | 5/2011 | Nguyen et al. |
| 2011/0319933 A1 | 12/2011 | Tepic |
| 2012/0059384 A1 | 3/2012 | Fan et al. |
| 2012/0179163 A1 | 7/2012 | Housman et al. |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester et al. |
| 2013/0158610 A1 | 6/2013 | Hernandez |
| 2014/0142697 A1 | 5/2014 | Sklar et al. |
| 2014/0148850 A1 | 5/2014 | DiMatteo et al. |
| 2014/0277130 A1 | 9/2014 | Housman |

FOREIGN PATENT DOCUMENTS

| | | |
|---|---|---|
| CN | 101031248 A | 9/2007 |
| CN | 101422381 A | 5/2009 |
| CN | 101573078 A | 11/2009 |
| CN | 201436022 U | 4/2010 |
| CN | 102068305 A | 5/2011 |
| CN | 102512253 A | 6/2012 |
| CN | 102525583 A | 7/2012 |
| CN | 102551821 A | 7/2012 |
| CN | 102905636 A | 1/2013 |
| CN | 10253662 B | 2/2015 |
| EP | 0502698 B1 | 9/1992 |
| EP | 05202698 A1 | 9/1992 |
| EP | 0538895 A2 | 4/1993 |
| EP | 0682917 B1 | 11/1995 |
| EP | 0686373 A1 | 12/1995 |
| EP | 0669110 B1 | 5/2000 |
| EP | 1147751 B1 | 10/2001 |
| EP | 1093774 B1 | 6/2002 |
| EP | 1234637 A2 | 8/2002 |
| EP | 0796593 B1 | 5/2004 |
| EP | 1430843 A2 | 6/2004 |
| EP | 1917926 A1 | 7/2008 |
| EP | 2036501 A3 | 9/2010 |
| EP | 2422711 A1 | 2/2012 |
| EP | 2422712 A1 | 2/2012 |
| EP | 2422712 A2 | 2/2012 |
| EP | 2596758 A1 | 5/2013 |
| EP | 2601894 A1 | 6/2013 |
| FR | 2760355 A1 | 9/1998 |
| FR | 2803739 A1 | 7/2001 |
| FR | 284687 A1 | 5/2004 |
| FR | 2846867 A1 | 5/2004 |
| FR | 2879915 A1 | 6/2006 |
| GB | 2294399 A | 5/1996 |
| JP | H10-000200 | 1/1998 |
| JP | H10200 A | 1/1998 |
| JP | 2005-529650 | 10/2005 |
| JP | 2006-212449 A | 8/2006 |
| JP | 2006-305348 A | 11/2006 |
| WO | 9608205 A1 | 3/1996 |
| WO | 9619947 A1 | 7/1996 |
| WO | 9802117 A1 | 1/1998 |
| WO | 9826717 A1 | 6/1998 |
| WO | 03063713 A1 | 8/2003 |
| WO | 03103507 A2 | 12/2003 |
| WO | 2006055516 A2 | 5/2006 |
| WO | 2007093192 A1 | 8/2007 |
| WO | 2008021474 A2 | 2/2008 |
| WO | 2008100944 A1 | 8/2008 |
| WO | 2009042951 A1 | 4/2009 |
| WO | 2010009217 A1 | 1/2010 |
| WO | 2010017631 A1 | 2/2010 |
| WO | 2010053708 A1 | 5/2010 |
| WO | 2011059995 A2 | 5/2011 |

(56) References Cited

FOREIGN PATENT DOCUMENTS

| WO | 2011060022 A2 | 5/2011 |
|---|---|---|
| WO | 2011112776 A1 | 9/2011 |
| WO | 2012171011 A1 | 12/2012 |

OTHER PUBLICATIONS

International Search and Written Opinion for PCT/US2011/027837 mailed May 19, 2011.
International Search and Written Opinion for PCT/US2009/065304 mailed Jun. 5, 2013.
International Search and Written Opinion for PCT/US2012/041298 mailed Jun. 5, 2013.
International Search and Written Opinion for PCT/US2012/028803 mailed Oct. 24, 2010.
Notice of Reasons for Rejections for Japanese Patent Application No: 2011-538642, mailed Oct. 1, 2013.
First Office Action for Chinese Patent Application No: 200980155954.7, issued Apr. 12, 2013.
Second Office Action for Chinese Patent Application No. 200980155954.7, issued Oct. 24, 2013.
First Office Action for Chinese Patent Application No. 201180013194.3, issued Jul. 21, 2014.
Notice of Reasons for Rejection for Japanese Patent Application No. 2012-557236 mailed Nov. 25, 2014.
Patent Examination Report No. 1 for Australian Patent Application No. 2009319879 issued Nov. 10, 2014.
International Search and Written Opinion for PCT/US2014/066389 mailed Feb. 17, 2015.
Notice of Reasons for Rejection for Japanese Patent Application No. 2012-557236 mailed Mar. 2, 2015.
International Search Report and Written Opinion for PCT/2014/066389 mailed Feb. 17, 2015.
Patent Examination Report No. 1 for Australian Patent Application No. 2011224326 issued Apr. 21, 2015.
Second Office Action for Chinese Patent Application No. 201180013194.3, issued Mar. 23, 2015.
First Office Action for Chinese Patent Application No. 201280022627.6, issued Apr. 13, 2015.
International Preliminary Report for corresponding PCT Application No. PCT/US020747 mailed Sep. 17, 2015.
Second Office Action for related Chinese Patent Application No. 201280022627.6 issued Sep. 16, 2015.
Substantive Examination for related Mexican Patent Application No. MX/a/2013/010383 issued Aug. 12, 2015.
Patent Examination Report No. 1 for related Australian Patent Application No. 2012229152 Issued Aug. 18, 2015.
Third Office Action for related Chinese Patent Application No. 2011-80013194.3 issued Aug. 21, 2015.
International Preliminary Report on Patentability for related International Application No. PCT/US2014/033535, mailed Oct. 22, 2015.
Decision of Rejection on related Japanese Patent Application No. 2012-557236 mailed Oct. 9, 2015.
Communication from related European Patent Application No. 09761114.9 mailed Dec. 3, 2015.
Communication from related European Patent Application No. 11710940.5 mailed Dec. 8, 2015.
First Office Action for related Chinese Patent Application No. 201280038677.3 issued Sep. 6, 2015.
Patent Examination Report No. 1 for related Australian Patent Application No. 2012267924 mailed Dec. 22, 2015.
Substantive Examination Report from related Mexico Patent Application No. MX/a/2013/010383 mailed Jan. 19, 2016.
Notice of Reasons for Rejection for related Japanese Application No. 2013-558094 mailed Feb. 2, 2016.
Substantive Examination Report from related Russian Application No. 2013144961/14(069526) mailed Dec. 23, 2015.
Third Office Action from related Chines Application No. 201280022627.6 issued Mar. 4, 2016.
Second Office Action from related Chinese Application No. 201280038677.3 issued May 5, 2016.
International Preliminary Report on Patentability from related PCT Application No. PCT/US2014/066389 issued May 24, 2016.
Office Action from related Mexican Application No. MX/a/2013/010383 issued May 3, 2016.
Notice of Reasons for Rejection from related Japanese Application No. 2014-514625 issued Jun. 13, 2016.
Communication from EPO from related European Application No. 12711719.0-1666 issued Jul. 28, 2016.
International Search and Written Opinion for PCT/US2014/022539 mailed Jun. 27, 2014.
International Search and Written Opinion for PCT/US2014/020747 mailed Jun. 6, 2014.
Decision of Rejection for Japanese Patent Application No. 2011-538642, mailed Jun. 14, 2014.
International Search and Written Opinion for PCT/US2014/033535 mailed Jul. 18, 2014.
Decision of Rejection from related Japanese Application No. 2013-558094 issued Sep. 5, 2016.
Office Action from related Russian Application No. 2015147534120(073143) issued Jun. 29, 2016.
First Office Action from related Chinese Application No. 201480012203.0 issued Aug. 17, 2016.
Office Communication from related European Application No. 14712930.8 -1662 issued Nov. 24, 2016.
Office Action from related Japanese Application No. 2014-514625 issued Dec. 19, 2016.
Office Action and Search Report from related Chinese Application No. 201480032876.2 issued Oct. 19, 2016.
Third Office Action from related Chinese Application No. 201280038677.3 issued Nov. 28, 2016.

\* cited by examiner

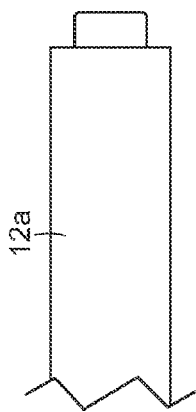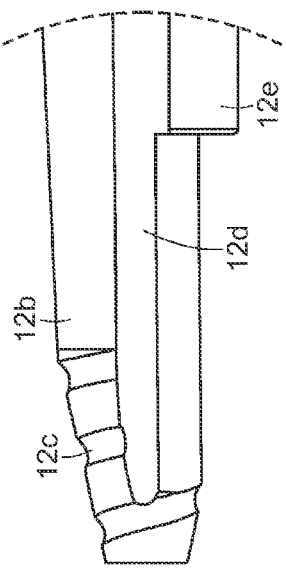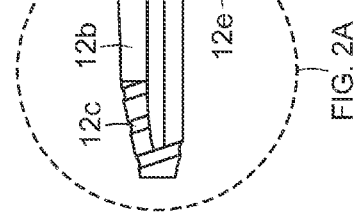

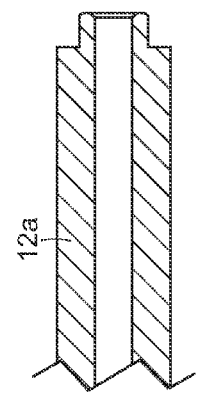
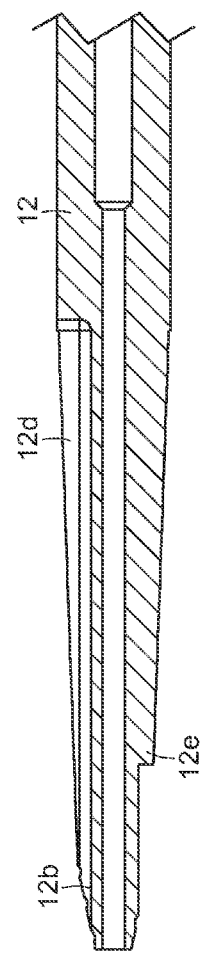
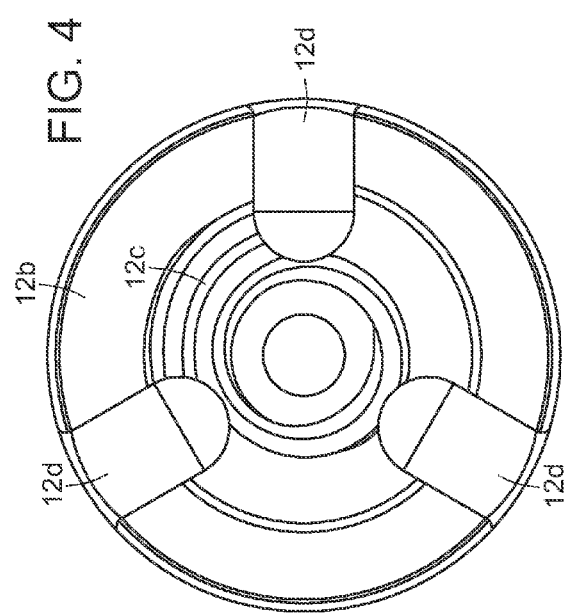
FIG. 3
FIG. 4

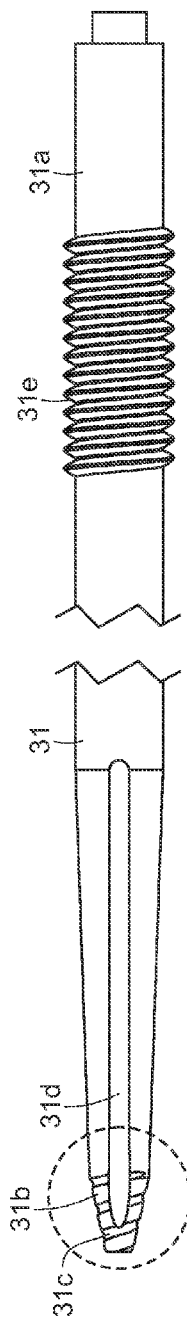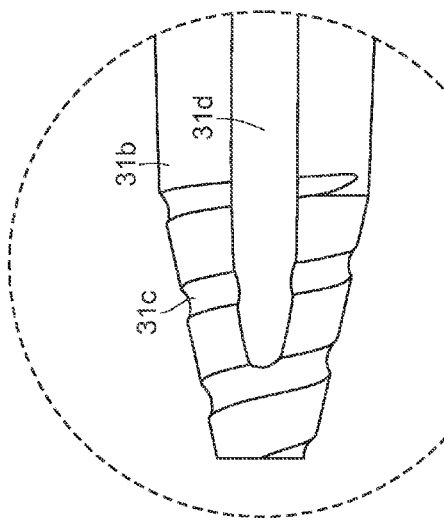
FIG. 9
FIG. 9A

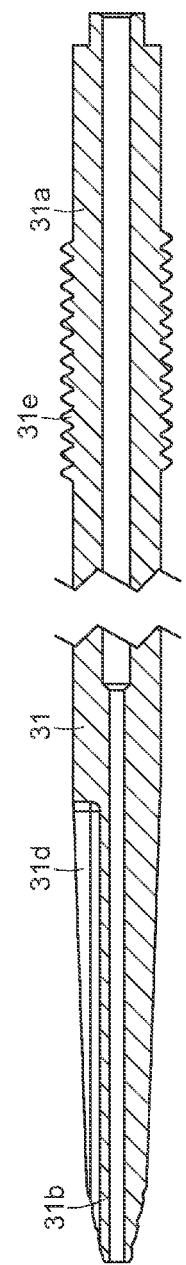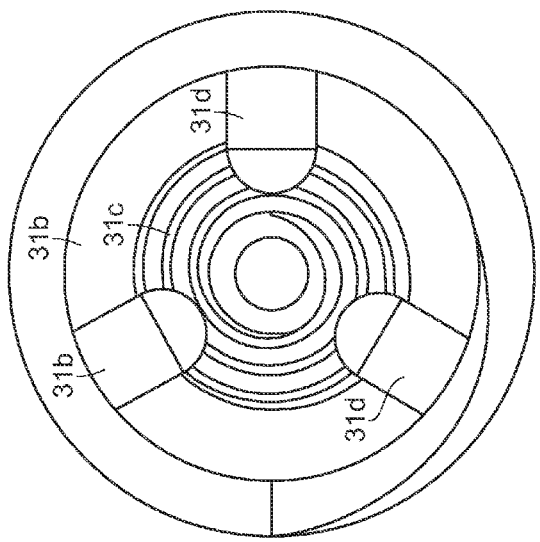
FIG. 10
FIG. 11

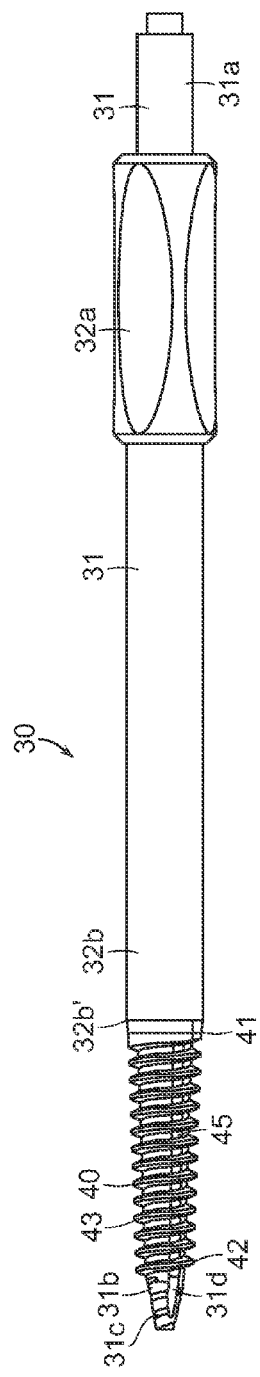
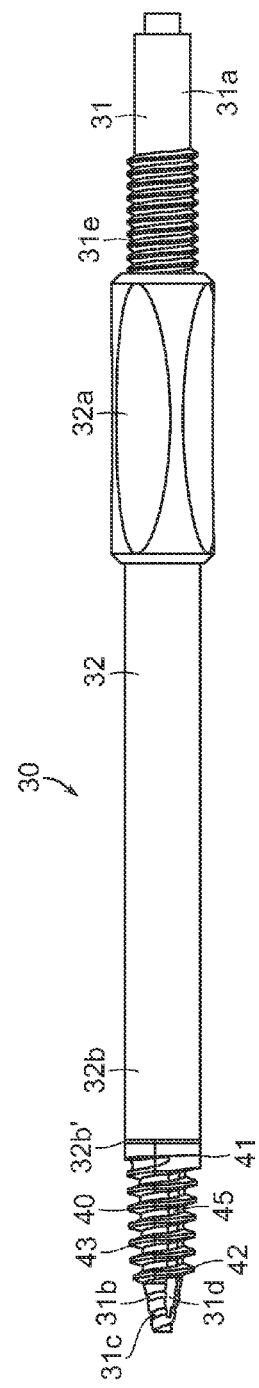

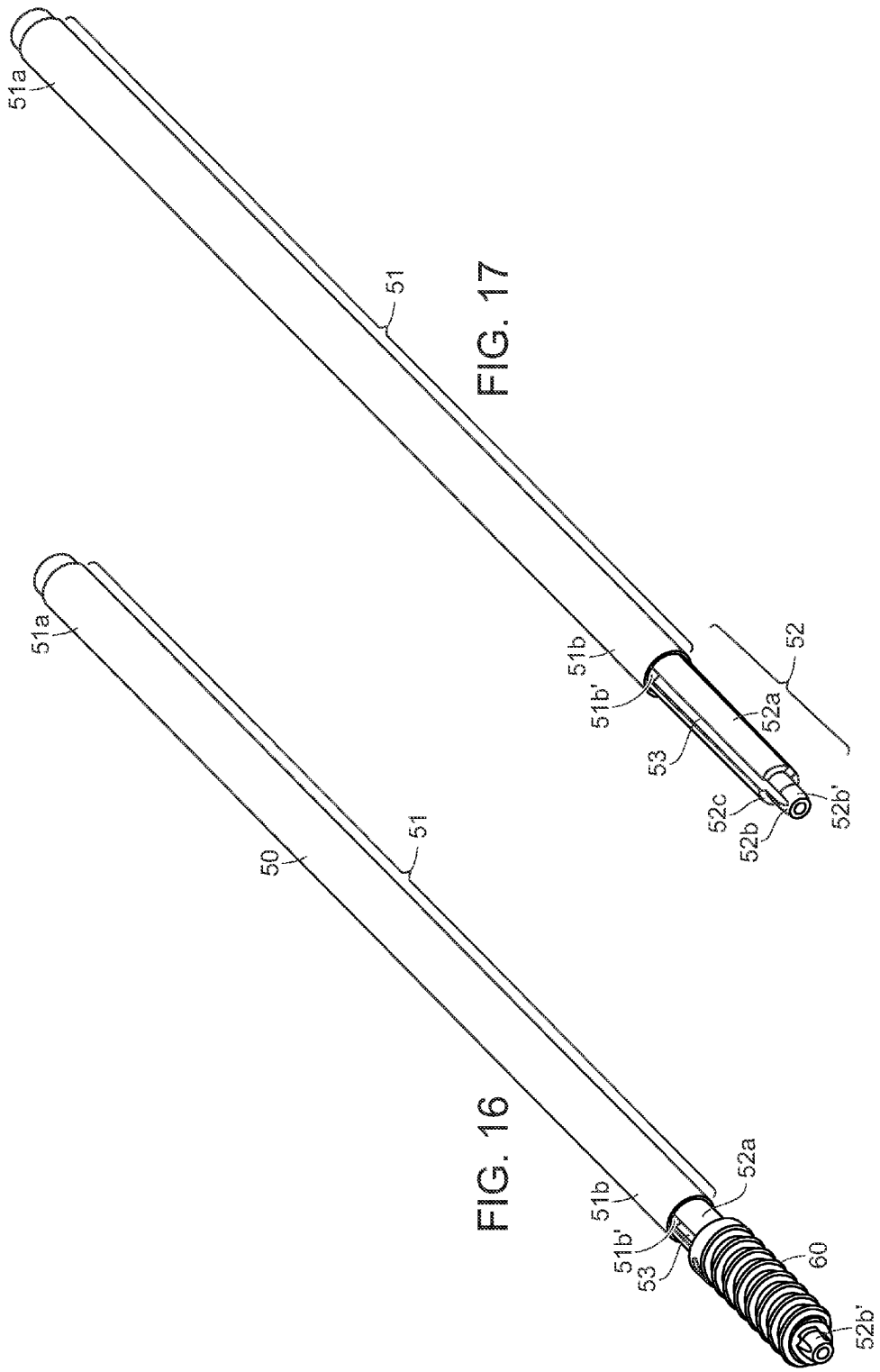

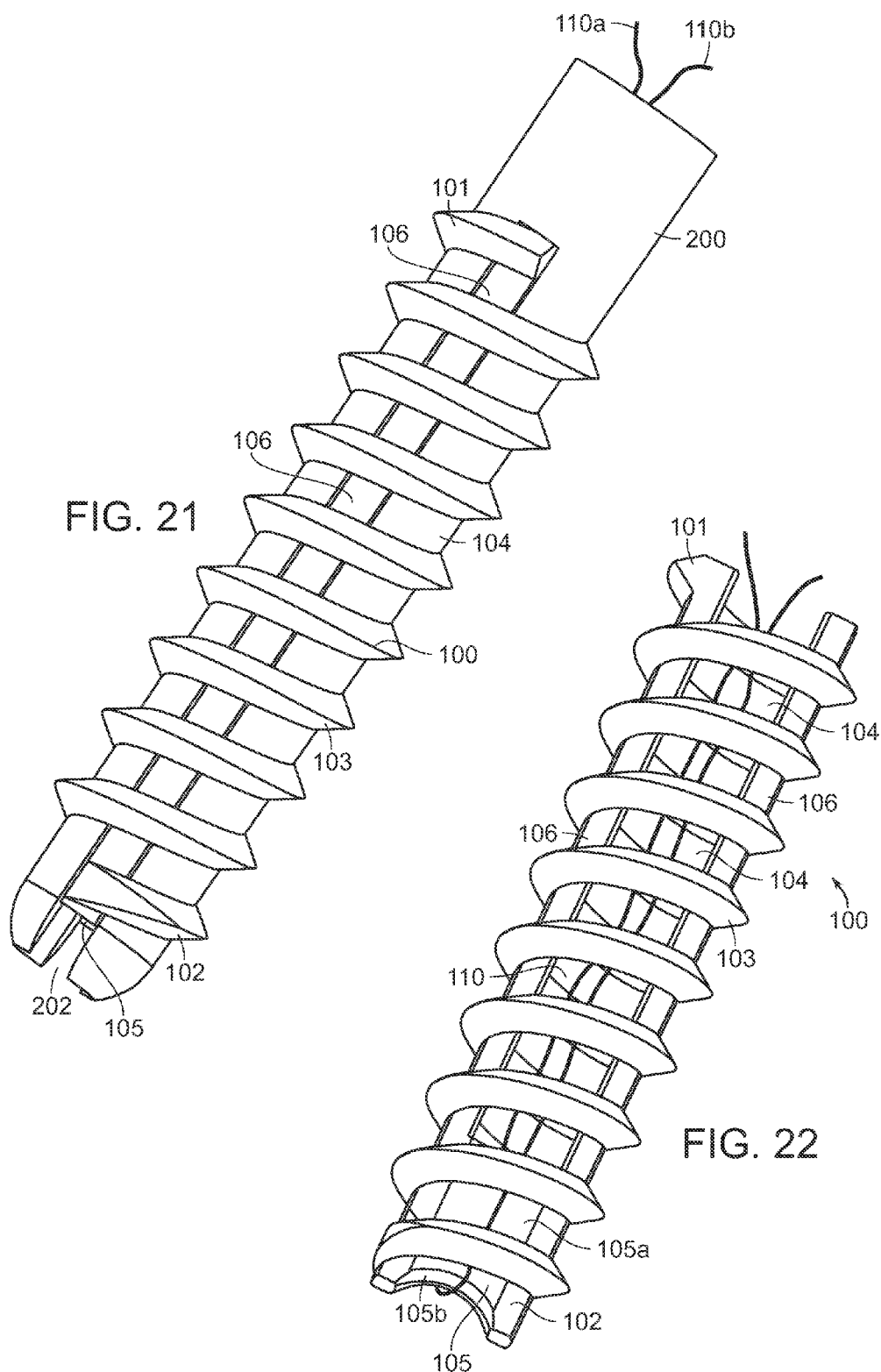

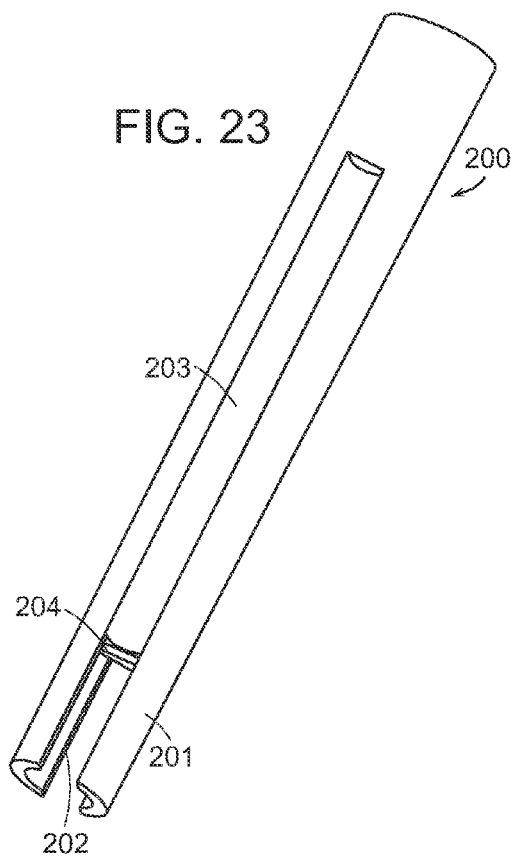
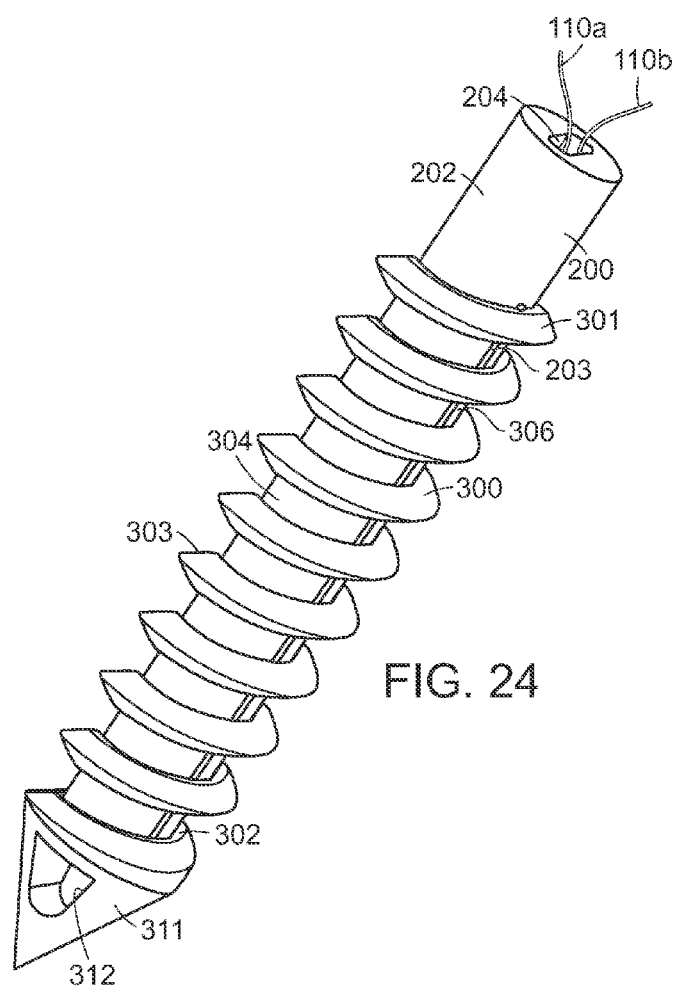

ANCHOR HAVING A CONTROLLED DRIVER ORIENTATION

CROSS-REFERENCE TO RELATED APPLICATIONS

This application is a continuation-in-part application of U.S. patent application Ser. No. 13/044,777 filed Mar. 10, 2011, which claims priority to U.S. Patent Application Ser. No. 61/312,291 filed Mar. 10, 2010, U.S. Patent Application Ser. No. 61/334,808, filed May 14, 2010 and U.S. Patent Application Ser. No. 61/359,080 Jun. 28, 2010 the disclosures of which are incorporated herein by reference in their entireties.

BACKGROUND

Field of Technology

The present disclosure relates to medical apparatuses and procedures in general, and more particularly to medical apparatuses and procedures for reconstructing a ligament.

Related Art

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon.

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel in a number of applications, such as ACL reconstruction surgery and biceps tenodesis. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to-ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY

In one aspect, the present disclosure relates to an interference screw. The screw includes a body having a proximal end, a distal end, and a longitudinal axis extending between the proximal end and distal end. The screw further includes threads extending in an open helical form between the proximal end and distal end of the body. The screw further includes a through bore defined by the body extending between the proximal end and distal end of the body along the longitudinal axis. The through bore has a surface from which a controlling member is formed. The controlling member being engaged by a driver when the driver is in a driving orientation with respect to the controlling member. The controlling member being not engaged by the driver when the driver is in an orientation different than the driving orientation.

In another aspect, the present disclosure relates to a method for installing an interference screw into bone. The method includes removing a driver from a body of an interference screw inserted into bone. The body has a proximal end, a distal end, and a longitudinal axis extending between the proximal end and distal end. The body defines a through bore extending between the proximal end and distal end along the longitudinal axis. The through bore has a surface. The method further includes engaging a controlling member formed by the surface of the through bore with the driver. The controlling member being engaged by the driver when the driver is in a driving orientation with respect to the controlling member. The controlling member not being engaged by the driver when the driver is in an orientation different than the driving orientation. The method further includes confirming the orientation of the driver in the body of the screw based on the engagement of the controlling member with the driver.

In yet another aspect, the present disclosure relates to another method for installing an interference screw into bone. The method includes inserting, initially, a driver into a through bore defined by a body of an screw inserted into bone. The through bore extends between a proximal end and a distal end of the body along a longitudinal axis extending between the proximal end and distal end of the body. The through bore has a surface. The method further includes rotating the driver within the through bore, about the longitudinal axis of the body, until the driver engages a controlling member formed by the surface of the through bore. The engagement confirms a driving orientation of the driver with respect to the controlling member. The method further includes driving the screw further into the bone with the driver in the driving orientation.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 2 shows a side view of the shaft of the delivery device of FIG. 1.

FIG. 2A shows an exploded view of the distal end of the shaft of FIG. 2.

FIG. 3 shows a cross-sectional view of the shaft of FIG. 2.

FIG. 4 shows a front view of the distal end of the shaft of FIG. 2.

FIG. 9 shows a side view of the inner member of the shaft of FIG. 8.

FIG. 9A shows an exploded view of the distal end of the inner member of FIG. 9.

FIG. 10 shows a cross-sectional view of the inner member of the shaft of FIG. 9.

FIG. 11 shows a front view of the distal end of the inner member of FIG. 9.

FIGS. 14 and 15 show side views of the shaft of FIG. 8 with the outer member in different positions.

FIG. 16 shows an isometric view of a third embodiment of a shaft of the present disclosure and a screw for use with the shaft.

FIG. 17 shows an isometric view of the shaft of FIG. 16.

FIG. 21 shows an isometric view of a fourth embodiment of a shaft of the present disclosure and a screw for use with the shaft.

FIG. 22 shows an isometric view of the screw of FIG. 21.

FIG. 23 shows an isometric view of the shaft of FIG. 21.

FIG. 24 shows an isometric view of the shaft of FIG. 21 and an alternative screw for use with the shaft.

DETAILED DESCRIPTION OF THE EMBODIMENTS

The following description of the preferred embodiment(s) is merely exemplary in nature and is in no way intended to limit the disclosure, its application, or uses.

Figure 1:
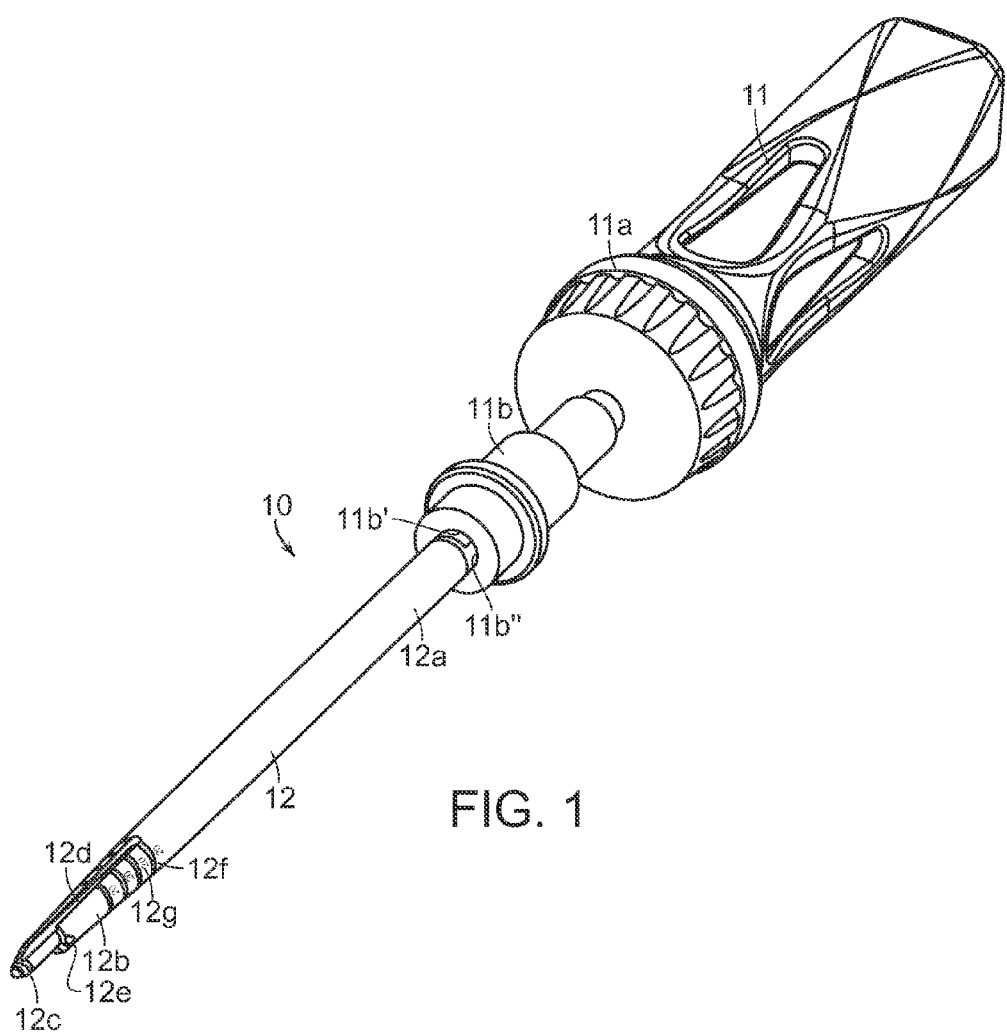
FIG. 1 shows a first embodiment of the delivery device of the present disclosure.

FIG. 1 shows a first embodiment of the delivery device 10 of the present disclosure. The device 10 includes a handle assembly 11 and a shaft 12 coupled to the handle assembly 11. The handle assembly 11 includes a handle 11a and a connector 11b coupled to the handle 11a. The connector 11b has a channel 11b' and an opening 11b" to the channel 11b'. The opening 11b" is in the shape of a "D". A proximal end 12a of the shaft 12 is disposed within the channel 11b'.

FIGS. 2, 2A, and 3-4 show the shaft 12. The shaft 12 includes a proximal end 12a and a distal end 12b. The proximal end 12a is in the shape of a "D" to match the shape of the opening 11b". The distal end 12b includes threads 12c, grooves 12d, and a depth stop 12e. The grooves 12d extend a partial length of the shaft 12 and intersect the threads 12c. The depth stop 12e is for use with a depth stop on a screw that the device 10 is used to implant into a bone tunnel during ligament reconstruction surgery.

Figure 5:
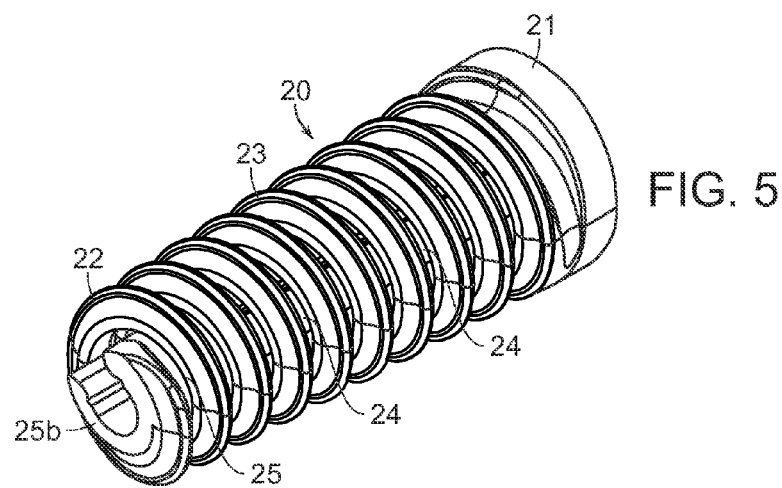
FIG. 5 shows an isometric view of the screw for use with the shaft of FIG. 2.
Figure 6:
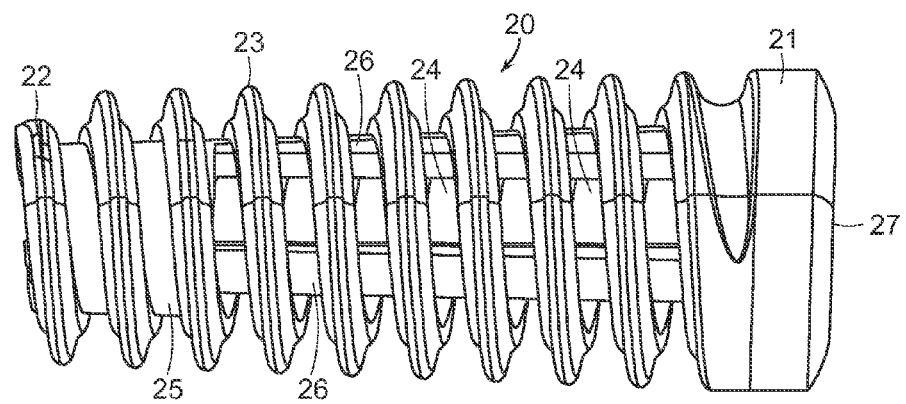
FIG. 6 shows a side view of the screw of FIG. 5.
Figure 7:
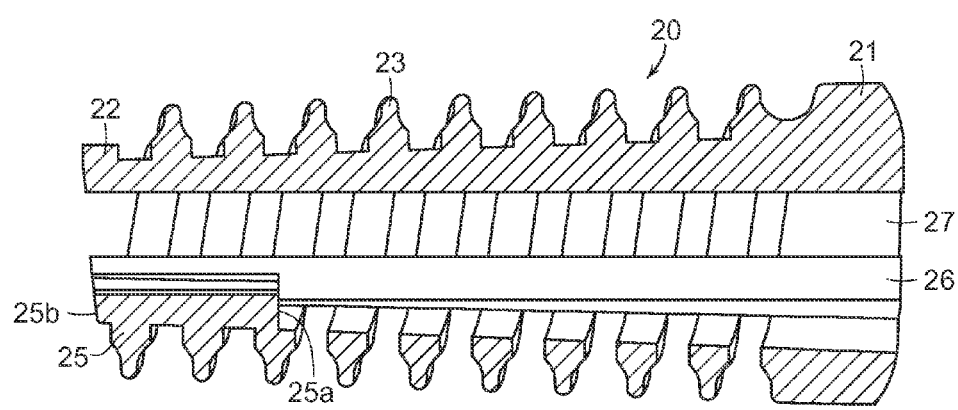
FIG. 7 shows a cross-sectional view of the screw of FIG. 6.
Figure 8:
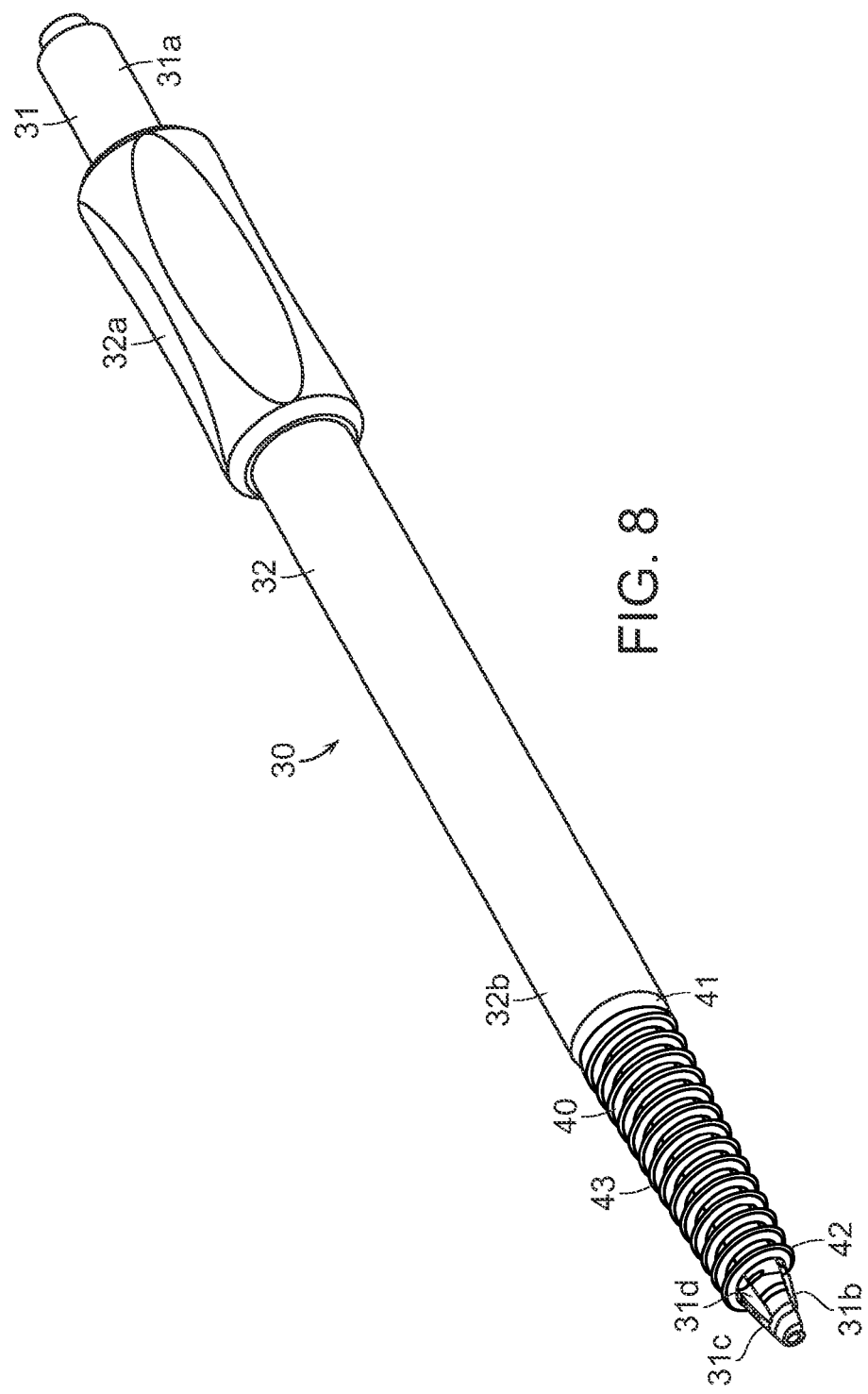
FIG. 8 shows a second embodiment of a shaft of the present disclosure.
Figure 12:
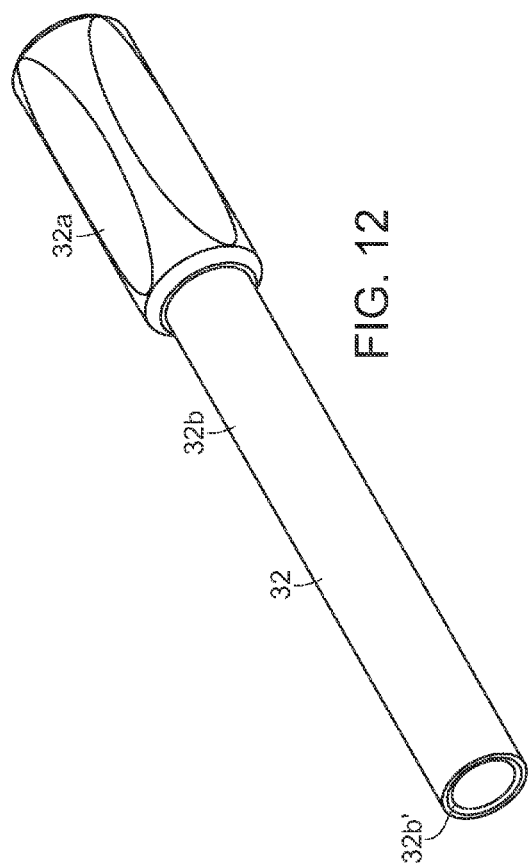
FIG. 12 shows an isometric view of the outer member of the shaft of FIG. 8.
Figure 13:
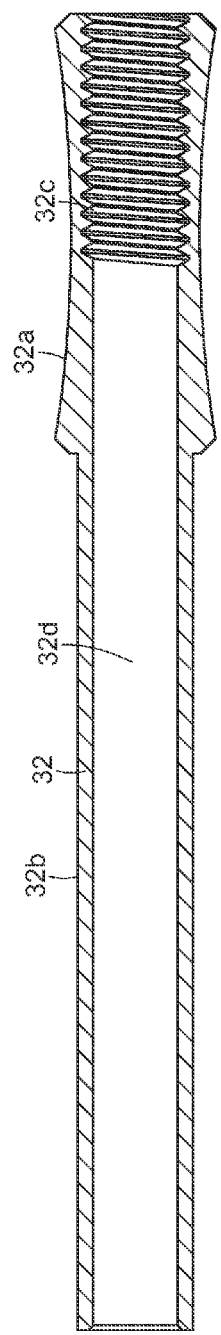
FIG. 13 shows a cross-sectional view of the outer member of FIG. 12.
Figure 18:
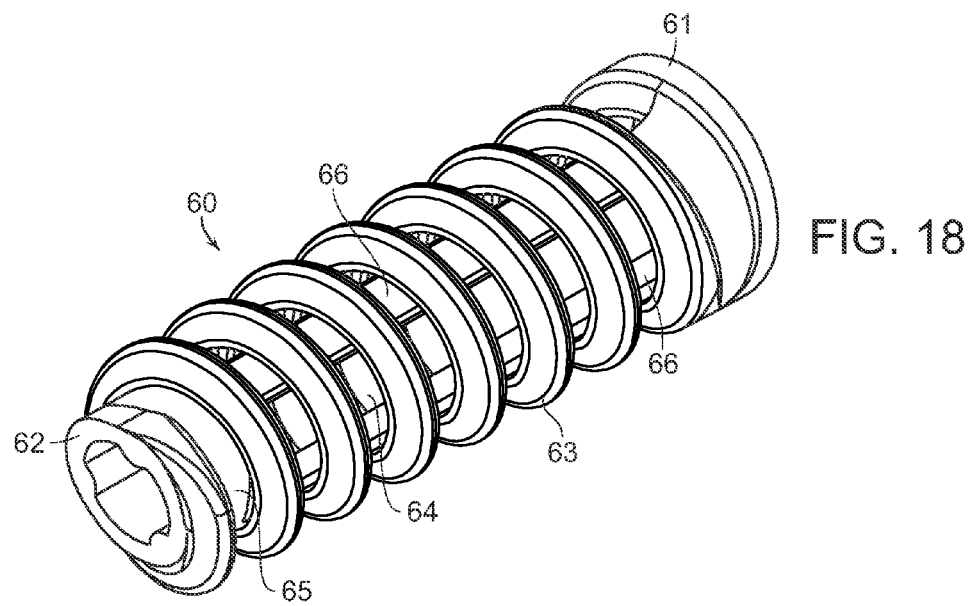
FIG. 18 shows an isometric view of the screw of FIG. 16.
Figure 19:
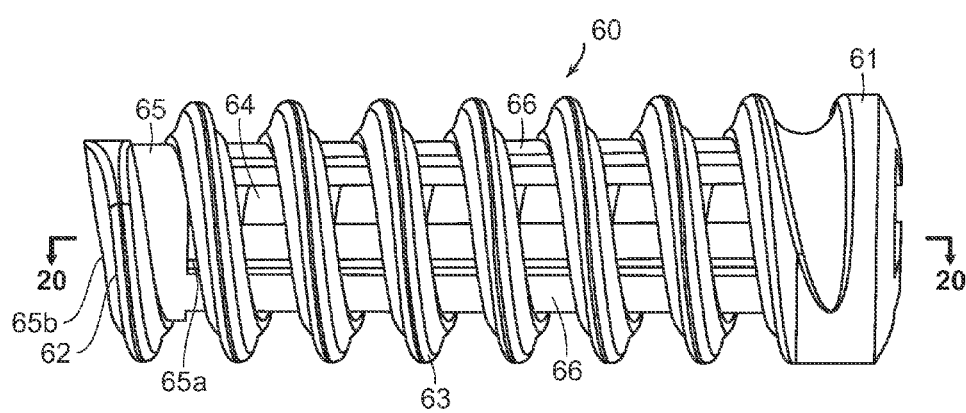
FIG. 19 shows a side view of the screw of FIG. 16.
Figure 20:
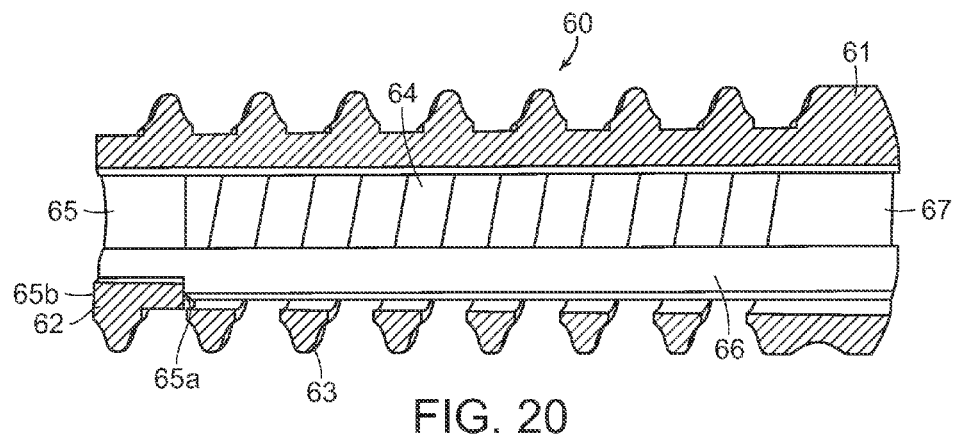
FIG. 20 shows a cross-sectional view of the screw of FIG. 19.

FIGS. 5-7 show the screw 20 for use with the delivery device 10 of the present disclosure. The screw 20 includes a proximal end 21 and a distal end 22. A majority of the screw 20 includes screw threads 23 in the form of an open helical coil, i.e. a connected series of continuous regularly spaced turns extending in a helical or spiral form substantially from the proximal end 21 to the distal end 22 with apertures 24 being defined by the space between the turns of the coil. In other words, interference screw 20 may include an open helical coil defining an internal volume, with the internal volume communicating with the region exterior to the open helical coil through the spacing between the turns of the open helical coil. The distal end 22 also includes a depth stop 25 that extends a partial length of the screw 20. The depth stop 25 includes a proximal end 25a and a distal end 25b. Additionally, a plurality of longitudinally-extending runners 26 extend along the interior of the screw threads 23.

The distal end 12b of the shaft 12 is placed within the interior of the screw 20, via the opening 27, until the proximal end 25a of the depth stop 25 engages the depth stop 12e of the shaft 12. During insertion of the shaft 12 into the screw 20, the runners 26 engage the grooves 12d and become housed within the grooves 12d. As shown in FIG. 1, the distal end 12b of the shaft 12 also includes hash marks 12f, each of which is associated with a number 12g. Once the screw 20 is placed on the shaft 12, the proximal end 21 of the screw 20 aligns with one of the hash marks/numbers 12f, thereby indicating the length of the screw 20.

FIGS. 8, 9-9A, and 10-15 show an alternative shaft 30 of the present disclosure. The shaft 30 includes an inner member 31 and an outer member 32 disposed over the inner member 31. The proximal end 31a of the inner member 31 is similar in shape to the proximal end 12a of the shaft 12. The distal end 31b of the inner member 31 includes threads 31c. Grooves 31d extend along the member 31 and intersect the threads 31c. Additionally, threads 31e are located between the proximal and distal ends 31a,31b of the member 31. The outer member 32 includes a first section 32a and a second section 32b. The first section 32a has a larger diameter than the second section 32b. The first section 32a also includes threads 32c on an inner wall 32d of the outer member 32.

Once the outer member 32 is disposed over the inner member 31, threads 32c engage threads 31e to move the outer member 32 relative to the inner member 31. Moving the outer member 32 relative to the inner member 31 allows for more or less of the distal end 31b of the inner member 31 to be shown. Similar to the distal end 12b of the shaft 12, the distal end 31b of inner member 31 includes hash marks/numbers (not shown) that align with an end 32b' of the second section 32b, thereby indicating a length of screw 40 that will be disposed on the distal end 31b of the inner member 31. As shown in FIGS. 14 and 15, the outer member 32 is located at different positions along the length of the inner member 31 to allow for screws 40 of different lengths to be loaded on the distal end 31b of the inner member 31.

A handle assembly, similar to the handle assembly 11, is coupled to the proximal end 31a of the inner member 31. Similar to screw 20, screw 40 includes a proximal end 41 and a distal end 42. The screw 40 includes screw threads 43 in the form of an open helical coil having an interior and a plurality of longitudinally-extending runners 45 extending along the interior of the screw threads 43. Screw 40 is more fully described in United States Patent Application Publication No. 20080154314, the disclosure of which is incorporated herein by reference in its entirety. Once the outer member 32 has been moved to indicate the screw length, the screw 40 is loaded onto the distal end 31b, such that a proximal end 41 of the screw 40 engages the end 32b' and the runners 45 engage the grooves 31d and become housed within the grooves 31d.

FIGS. 16-20 show another alternative embodiment of the shaft 50 and screw 60 of the present disclosure. The shaft 50 includes a first portion 51 including a proximal end 51a and a distal end 51b and a second portion 52 including a first area 52a and a second area 52b. The proximal end 51a is configured to be coupled to a handle assembly, similar to the handle assembly 11. However, other handle assemblies may be used. The first area 52a has a smaller diameter than the first portion 51, such that a first depth stop 51b' exists at the distal end 51b of the first portion 51. The second area 52b has a smaller diameter than the first area 52a such that a second depth stop 52c exists between the first area 52a and the second area 52b. An end 52b' of the second area 52b is tapered to allow for easier insertion of the anchor 60 into a bone during ligament reconstruction surgery, as will be further described below. The second portion 52 also includes grooves 53 extending between the first and second areas 52a,52b. For the purposes of this disclosure, there are three grooves 53. However, the second portion 52 may include a higher or lower number of grooves 53.

Similar to screw 20 shown in FIGS. 5-7, screw 60 includes a proximal end 61 and a distal end 62. A majority of the screw 60 includes screw threads 63 in the form of an open helical coil, i.e. a connected series of continuous regularly spaced turns extending in a helical or spiral form substantially from the proximal end 61 to the distal end 62 with apertures 64 being defined by the space between the turns of the coil. In other words, interference screw 60 may include an open helical coil defining an internal volume, with the internal volume communicating with the region exterior to the open helical coil through the spacing between the turns of the open helical coil. The distal end 62 also includes a depth stop 65 that extends a partial length of the screw 60. The depth stop 65 includes a proximal end 65a and a distal end 65b. Unlike the open depth stop 25 of screw 20 most clearly shown in FIG. 5, the depth stop 65 of screw 60 is a closed depth stop, most clearly shown in FIG. 18. Additionally, a plurality of longitudinally-extending runners 66 extend along the interior of the screw threads 63.

The second portion 52 of the shaft 50 is placed within the interior of the screw 60, via the opening 67, until the proximal end 65a of the depth stop 65 engages the second depth stop 52c of the shaft 50. During insertion of the shaft 50 into the screw 60, the runners 66 engage the grooves 53 and become housed within the grooves 53. The screws 60 may be of a variety of lengths. For example, a screw 60 may be of such length that its proximal end 61 would engage the first depth stop 51*b*'.

As described above, during ligament reconstruction surgery, the end of the graft ligament is placed in the bone tunnel and then the interference screw 20,40,60 is advanced into the bone tunnel via the use of shafts 12,30,50 so that the interference screw 20,40,60 extends parallel to the bone tunnel and simultaneously engages both the graft ligament and the side wall of the bone tunnel. The screws 20,40,60 may be used in either the femoral or tibial tunnels. Methods of ligament reconstruction via use of the screws 20,40,60 is further shown in the '314 publication shown above.

FIGS. 21-23 show yet another alternative embodiment of the screw 100 and the delivery device 200 of the present disclosure. The screw 100 includes a proximal end 101 and a distal end 102. A majority of the screw 100 includes screw threads 103 in the form of an open helical coil, i.e. a connected series of continuous regularly spaced turns extending in a helical or spiral form substantially from the proximal end 101 to the distal end 102 with apertures 104 being defined by the space between the turns of the coil. In other words, interference screw 100 may include an open helical coil defining an internal volume, with the internal volume communicating with the region exterior to the open helical coil through the spacing between the turns of the open helical coil. The distal end 102 also includes a suture bridge 105 that extends a partial length of the screw 100. The suture bridge 105 includes a proximal end 105*a* and a distal end 105*b*. The distal end 105*b* includes a concave shape. A flexible member 110, such as a suture, is housed within the screw 100, such that the suture 110 extends around the distal end 105*b* of the bridge 105. Additionally, longitudinally-extending runners 106 extend from the suture bridge 105 and along the interior of the screw threads 103. For the purposes of this disclosure, there are two longitudinally extending runners 106. However, more or less than two runners are within the scope of this disclosure.

The delivery device 200 includes a distal end 201 having a slot 202 and grooves 203 extending from the slot 202 on each side of the device 200. As shown in FIG. 21, the screw 100 is located on the distal end 201 such that the suture bridge 105 is housed within the slot 202 and the runners 106 are housed within the grooves 203. The delivery device 200 is cannulated, such that when the screw 100 is located on the device 200, the suture ends 110*a*,110*b* extend through the cannulation 204.

Figure 25:
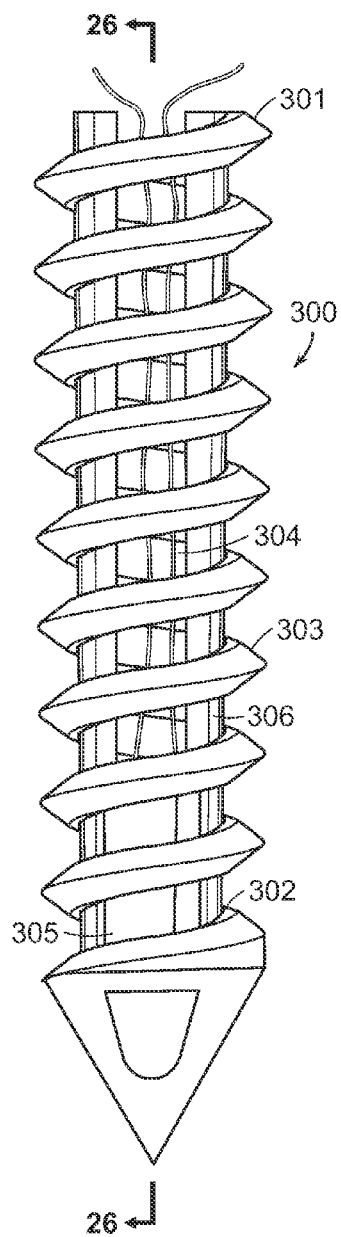
FIG. 25 shows a side view of the screw of FIG. 24.
Figure 26:
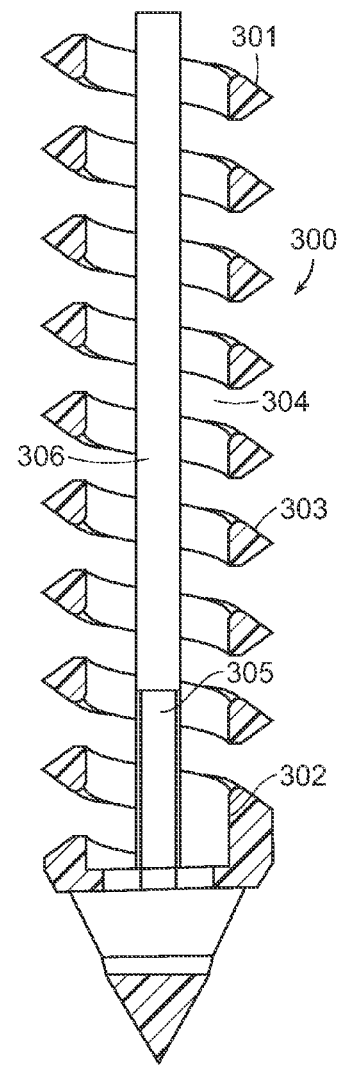
FIG. 26 shows a cross-sectional view of the screw of FIG. 24.

FIGS. 24-26 show a screw 300 similar to screw 100. However, screw 300 additionally includes a pointed tip 311 located on the distal end 302. The tip 311 includes a through hole 312. The hole 312 helps in locating the suture 110 within the interior of the screw 300. As shown in FIG. 24, the screw 300 is located on the distal end 201 of delivery device 200 such that the suture bridge 305 is housed within the slot 202 and the runners 306 are housed within the grooves 203. As stated above, the delivery device 200 is cannulated, such that when the screw 300 is located on the device 200, the suture ends 110*a*,110*b* extend through the cannulation 204, as shown in FIG. 24.

For clarity purposes, only the distal end 201 of the device 200 is shown. However, the device 200 would include a proximal end, similar to the devices above, which may be coupled to a handle assembly, similar to handle assembly 11 above. The screws 100,300 are used in the repair of soft tissue, specifically to re-attach tissue to bone. One example of this repair is when the screw 100,300 is delivered into bone via the use of device 200, the device 200 is removed from screw 100,300, the tissue is placed on the bone to be adjacent the screw 100,300, the suture ends 110*a*,110*b* are pulled through the tissue, and then the suture ends 110*a*,110*b* are tied. A hole may be made in the bone prior to insertion of the screw 100,300 into the bone. However, screw 300 may be inserted into bone without first making a hole in the bone. In this case, the pointed tip 311 is used to start insertion of the screw 300 into the bone and then rotary motion may be used to complete insertion of the screw 300 into the bone. Other methods of tissue repair via use of these screws and delivery device may also be used.

The handle 11*a* of handle assembly 11 is made from plastic, however, other non-metal and metal materials may also be used. The shape and size of handle 11*a* may be any shape and size necessary to help facilitate insertion of the screw 20 into bone. The coupler 11*b* is made from a metal material, such as stainless steel or titanium, but may be made from other metal and non-metal materials that are strong enough to withstand the forces applied during surgery. The coupler 11*b* is press-fit to the handle 11*a*, but may be coupled to the handle 11*a* in any other manner known to those of skill in the art. The size and shape of the coupler 11*b* may be any size and shape necessary to help facilitate insertion of the screw 20 into bone. The channel 11*b*' may be any length necessary and the opening 11*b*" may be any shape necessary to facilitate coupling of the shaft 12 to the coupler 11*b*.

The shaft 12 is made from a metal material, such as stainless steel and titanium, however, other metal and non-metal materials that would withstand the forces applied during surgery may be used. The diameter of the shaft 12 may vary. The proximal end 12*a* of the shaft 12 may be any shape necessary to facilitate insertion of the end 12*a* through opening 11*b*" and into channel 11*b*'. The number of threads 12*c* and grooves 12*d* may vary and the lengths of the grooves 12*d* may also vary. The location of depth stop 12*e* may also vary based on the diameter of the shaft 12 and the diameter of the screw 20 that is used. The grooves 12*d*, depth stop 12*e*, and threads 12*c* may be formed by any method known to one of skill in the art.

The screw 20 is made from a polymer material via a molding method. However, other material, which would allow the screw 20 to withstand forces applied during surgery, and other methods of making may be used. The depth stop 25 is open ended and doesn't extend the entire inner diameter of the screw 20. The amount of screw inner diameter that the depth stop 25 covers may vary and the length of the depth stop 25 may vary based on the diameter of the screw. The number and length of the runners 26 may also vary. Once the screw 20 is located on the shaft 12, the distal end 12*b* of the shaft 12 extends from the distal end 22 of the screw 20. During insertion of the screw 20 into bone, the threads 12*c* create threads in the bone, thereby creating a seat for the screw threads 23, as described more fully in the '314 publication. The amount of the distal end 12*b* of the shaft 12 that extends from the distal end 22 of the screw 20 may vary.

The diameters of the first and second sections 32*a*,32*b* of outer member 32 may vary and the number of threads 32*c* may also vary. The number of threads 31*c*,31*e* and grooves 31*d* may vary and the lengths of the grooves 31*d* may also vary. The inner and outer members 31,32 are made from a metal material, such as stainless steel and titanium, and via a method known to one of skill in the art. However, other materials may also be used. The screw 40 is made from a polymer material via a molding method. However, other material and methods of making may be used. The number and length of the runners 45 may also vary. Once the screw 40 is located on the shaft 30, the distal end 31b of the shaft 30 extends from the distal end 42 of the screw 40. During insertion of the screw 40 into bone, the threads 31c create threads in the bone, thereby creating a seat for the screw threads 43, as described more fully in the '314 publication. The amount of the distal end 31b of the shaft 30 extending from the screw 40 may vary.

The shaft 50 is made from a metal material, such as stainless steel or titanium, but may be made from another metal material or a non-metal material that is strong enough to withstand the force applied to the shaft 50 during surgery. The shaft 50 may be made via a method known to one of skill in the art. The diameters of the first and second portions 51,52 may vary along with the number and lengths of the grooves 53 and the locations of the depth stops 52c,51b' may vary based on the diameter of the screw 60 or other factors. Rather than being tapered, the end 52b' may be designed in another manner to allow easier insertion of the screw 60 into bone. The screw 60 is made from a polymer material via a molding method. However, other material, which would allow the screw to withstand the forces applied during surgery, and other methods of making may be used. The number and length of the runners 66 may also vary. Once the screw 60 is located on the shaft 50, the second portion 52 of the shaft 50 extends from the distal end 62 of the screw 60. The amount of the second portion 52 extending from the screw 60 may vary. Additionally, the length of the depth stop 65 may also vary based on the diameter of the screw 60 or other factors.

The delivery device 200 is made from a metal material, such as stainless steel or titanium, but may be made from a non-metal material that is strong enough to withstand the forces applied to the device 200 during surgery. The delivery device 200 is made via a method known to one of skill in the art. The screws 100,300 are made from a polymer material and via a molding process, however, other material, which would allow the screw to withstand the forces applied during surgery, and other processes known to one of skill in the art may be used. The suture bridge 105 may have a distal end 105b having a shape other than concave and the length of the suture bridge 105, the slot 202, and the grooves 203 may vary. The size and the shape of the hole 312 may vary.

Figure 27:
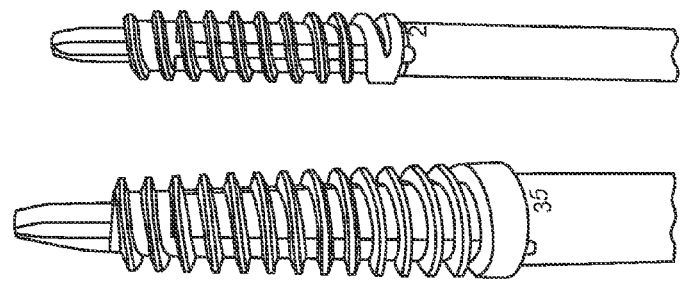
FIG. 27 shows a side view of an interference screw the entire length of which is supported by a driver.
Figure 28:
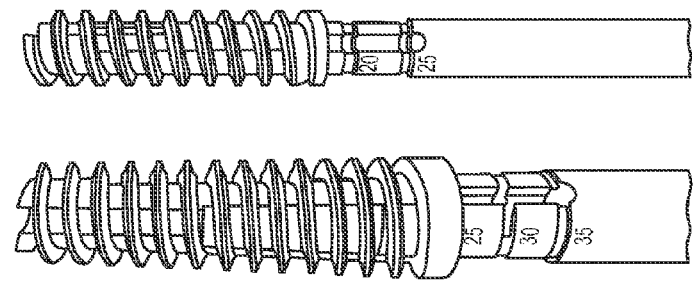
FIG. 28 shows a side view of an interference screw the entire length of which is not supported by a driver.
Figure 29:
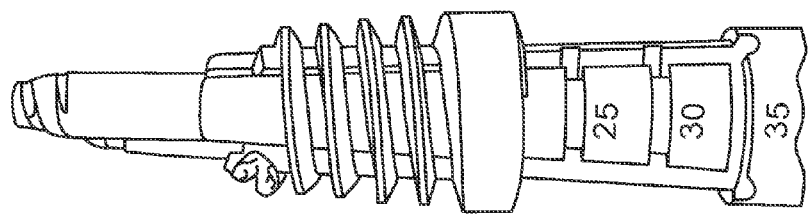
FIG. 29 shows a side view of an interference screw that has failed, structurally.

With some interference screw designs, it is necessary to support the entire length of an screw (or a substantial portion thereof) with a driver, as shown in FIG. 27, in order to insert the screw into bone properly. The need is especially great when the screw is made from a weak and/or brittle material, such as an osteoconductive material. This is also prevalent when the screw has fenestrations or openings that reduce the flexural (torsional) strength of the screw. Inserting the screw into bone when it is not fully supported, as shown in FIG. 28, may result in the screw failing, as shown in FIG. 29. With some screw designs, the orientation of the driver with respect to the screw determines whether the screw is fully supported or not. Accordingly, in these designs, there is a need to control the orientation of the driver with respect to the screw.

It may not be possible or it may be difficult for a surgeon to see the screw and/or driver and confirm the orientation of the driver with respect to the screw. For example, a surgeon's view may be obstructed when the screw is partly installed in bone. Accordingly, there is a further need to confirm the orientation of the driver with respect to the screw blindly.

Figure 30A:
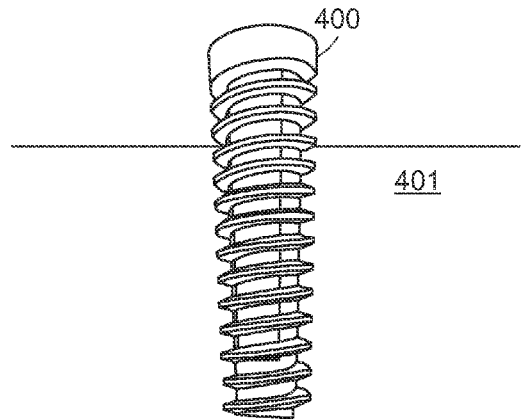
FIGS. 30A-30C show an example of an interference screw with a controlling member being inserted further into bone.
Figure 30B:
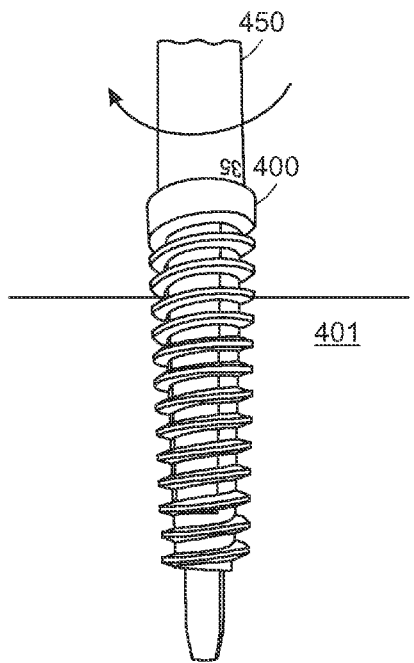
Figure 30C:
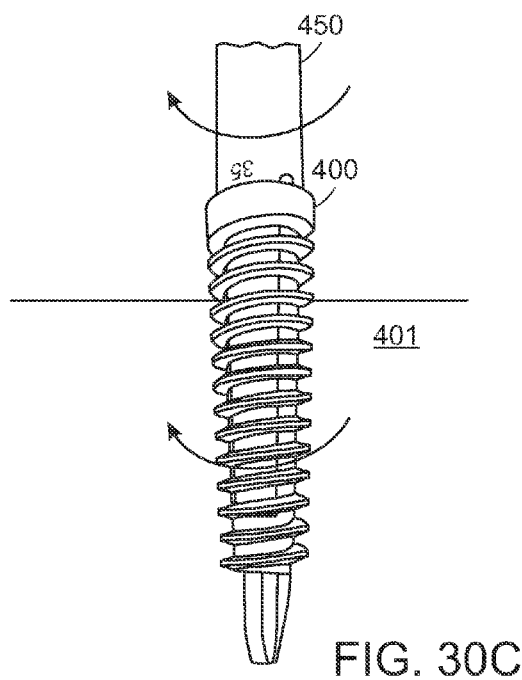

FIGS. 30A-C show the surgeon driving an example of an screw 400 with a controlling member into bone 401. As shown, the screw 400 sits proud of the surface of the bone 401. The surgeon drives the screw 400 further into the bone 401, so that it sits flush with the bone surface, by inserting a driver 450 into the screw 400. The surgeon then rotates of the driver 450 within the screw 400 until it engages the controlling member of the screw 400. Engagement of the driver 450 with the controlling member confirms that the driver 450 is in the proper "driving" orientation and provides the surgeon with the confidence that the screw 400 is fully supported by the driver 450. The surgeon can then drive the screw 400 into the bone 401 without worry of the screw 400 failing.

Figure 31:
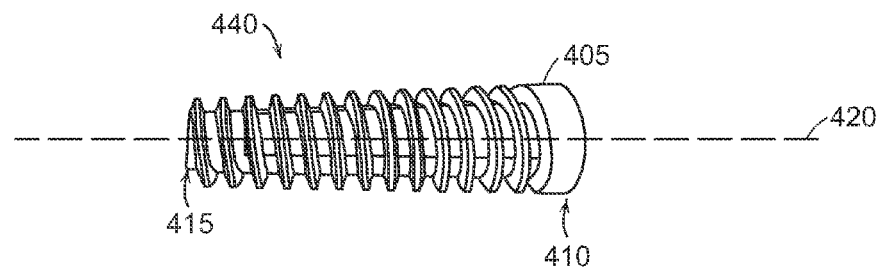
FIG. 31 shows a side view of an example of the interference screw with the controlling member.

FIG. 31 shows an example of the screw 400 having a body 405. The body 405 includes a proximal end 410, distal end 415, and longitudinal axis 420 extending between the proximal and distal ends 410, 415. The body 405 may be made from a bioabsorbable, non-bioabsorbable, osteoconductive or composite material. Examples of a non-bioabsorbable material include polyether ether ketone (PEEK), titanium, and surgical stainless steel. The screw 400 further includes threads 425 extending in an open helical form between the proximal end 410 and distal end 415 of the body 405. In some examples of the screw 400, the threads 425 are similar to the threads 63 described above with reference FIGS. 5-7.

Figure 32:
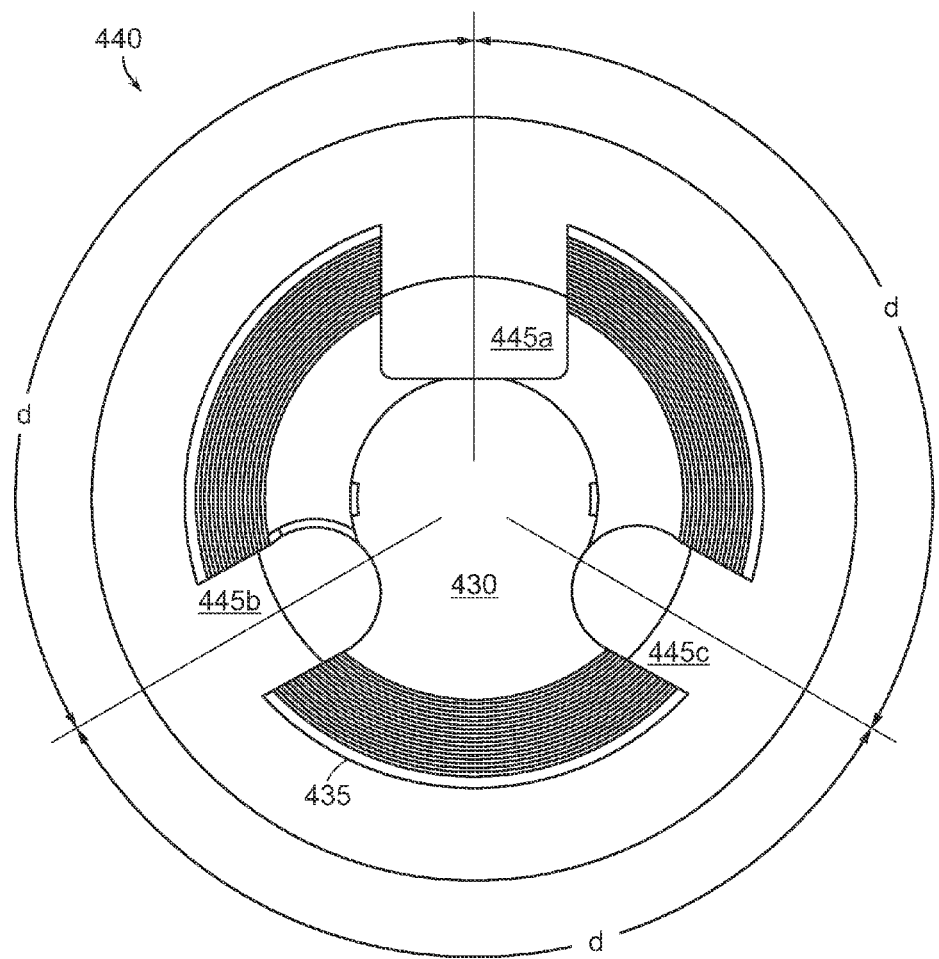
FIG. 32 shows an end view of an example of the interference screw with the controlling member.

FIG. 32 shows the body 405 defining a through bore 430. The through bore 430 extends between the proximal and distal ends 410, 415 of the body along the longitudinal axis 420. The through bore 430 has a surface 435. The screw 400 includes a controlling member 440 formed by the through bore surface 435. The driver 450 engages the controlling member 440 when the driver 450 is in a driving orientation with respect to the screw 400. The driver 450 does not engage the controlling member 440 when the driver 450 is in an orientation different than the driving orientation.

One example of the controlling member 440 shown in FIG. 32 includes a plurality of runners 445 extending between the proximal and distal ends 410, 415 of the body 405 along the longitudinal axis 420. Three runners (445a, 445b, 445c) are shown but other multiples of runners are possible (e.g., two and four). The plurality of runners 445 is spaced equally around the circumference of the through bore 430. There is an equal distance (d) between each of the runners (445a, 445b, 445c) (the distance (d) being measured, for example, from centerline to centerline of each of the runners). The runners (445a, 445b, 445c) can be described as being arranged in a radial manner about the longitudinal axis 420 (coming out of the page of the figure). As such, the position of each of the runners (445a, 445b, 445c) can be described as being at 0° (12 o'clock), at 120° (4 o'clock), and at 240° (8 o'clock), respectively.

One of the plurality of runners is of different shape and/or size than the other runners. A convenient example of the controlling member 440 includes one runner (445a) having a cross sectional shape based on a rectangle and the other runners (445b, 445c) having a cross sectional shape based on a semi-circle. Other cross sectional shapes are possible. In another example of the controlling member 440, the dimension(s) of one or more of the runners (445a, 445b, 445c), for example the width and/or height, varies with the overall size of the screw 400. For example, a first anchor is larger in size than a second anchor. In the first anchor, the height of runners is taller than the height of runners associated with the second anchor.

Figure 33A:
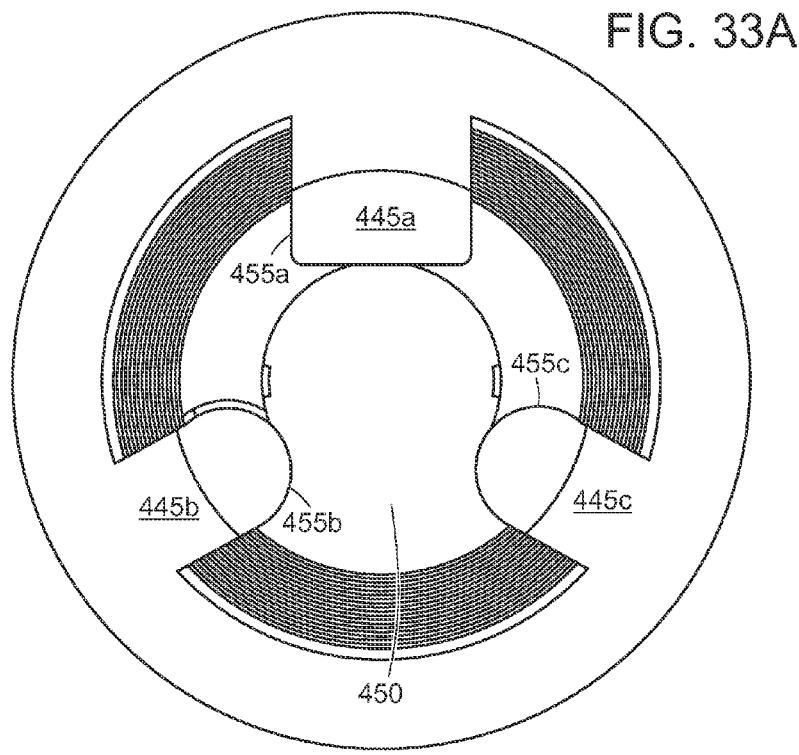
FIG. 33A shows a top view of a cross section of a driver in a driving orientation with respect to the interference screw.
Figure 33B:
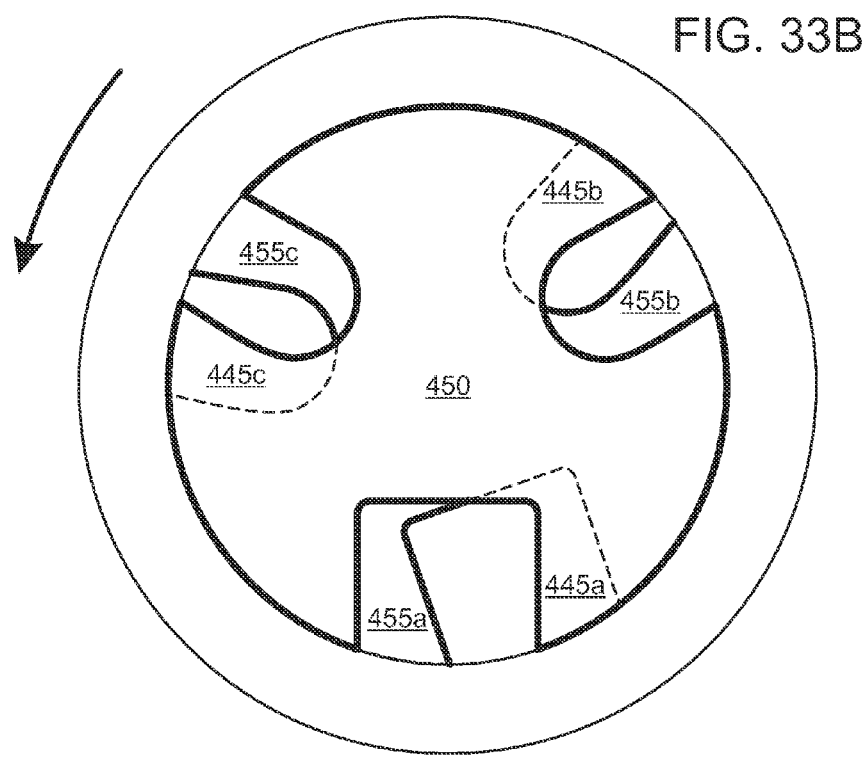
FIG. 33B shows a top view of a cross section of a driver in an orientation different then the driving orientation of FIG. 33A.

Turning now to FIGS. 33A-33B, which are views looking down at cross sections of the driver 450. The driver 450 used by the surgeon to turn the screw 400 into bone 401 includes grooves 455. The grooves 455 have an inverse geometry of the plurality of runners 445. When the driver 450 is in the driving orientation shown in FIG. 33A, the corresponding driver grooves 455 house the plurality of runners 445, thus, enabling the surgeon to turn the screw 400 using the driver 450. When the driver 450 is not in the driving orientation, as shown in FIG. 33B, the corresponding driver grooves 455 do not house the plurality of runners 445 (represented in the figure as hidden lines) and surgeon cannot turn the screw 400 using the driver 450. In the example shown in FIG. 33B, in order for the driver grooves 455 to house the plurality of runners 445, the driver is turned counterclockwise (in the direction of the drawn arrow), from the 10 o'clock to 9 o'clock position.

The foregoing arrangement provides a "one-way" engagement that is advantageous because the surgeon can control and confirm the orientation of the driver 450 without seeing the driver 450 and/or screw 400 i.e., the procedure can be done blindly. If the surgeon inserts the driver 450 into the screw 400 and is able to rotate it freely (i.e., without resistance) or is not able to insert the driver 450 into the screw 400 at all, then the surgeon knows that the driver 450 is not in the driving orientation. The surgeon can then rotate the driver 450 until it engages the controlling member 440 of the screw 400. Engaging the controlling member 440 causes the screw 400 to be driven into the bone and consequently, the surgeon must turn the driver 450 harder. As such, advantageously some examples of the screw 400 provide tactile feedback that enables the surgeon to seek the proper driver orientation.

Figure 34A:
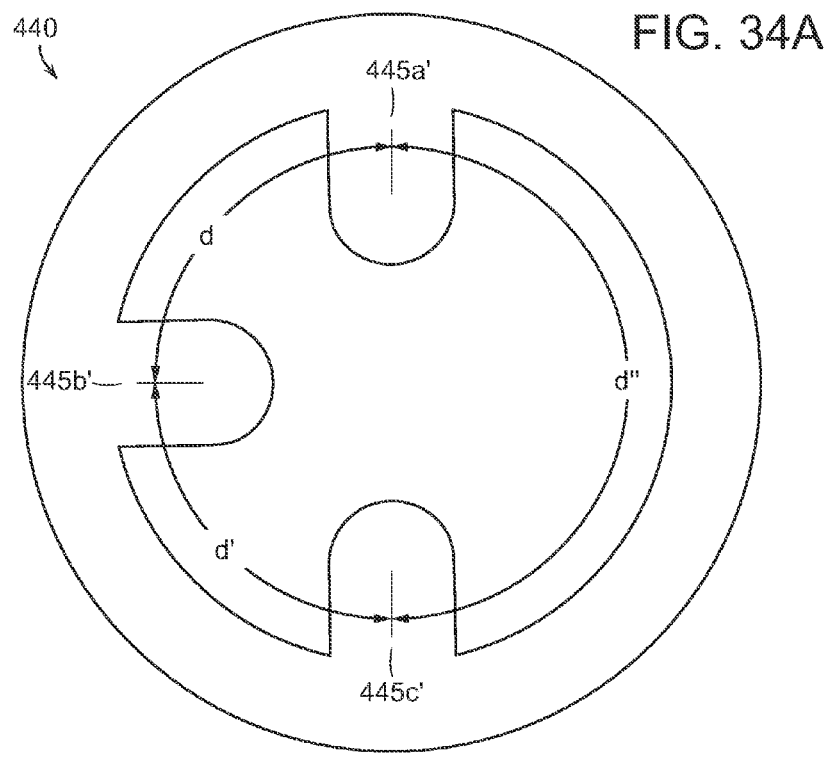
FIGS. 34A and 34B show examples of the controlling member.

FIG. 34A shows another example of the controlling member 440 that includes a plurality of runners 445' extending between the proximal and distal ends 410, 415 of the body 405 along the longitudinal axis 420. The plurality of runners 445' is spaced unequally around the circumference of the through bore 430. There is a different distance (d, d', d") between each of the runners 445' (the distances (d, d', d") being measured, for example, from centerline to centerline of each of the runners). Described in the terms of radial arrangement, the positions of the runners 445' are such that the number degrees separating positions are not equal.

Figure 34B:
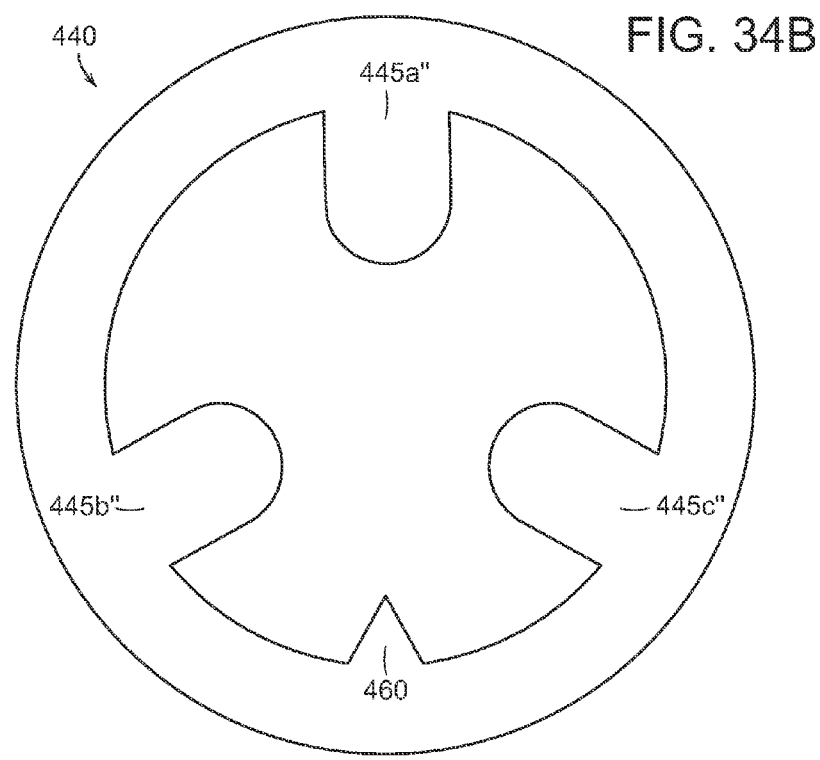

FIG. 34B shows yet another example of the controlling member 445 that includes a plurality of runners 445" extending between the proximal and distal ends 410, 415 of the body 405 along the longitudinal axis 420. The plurality of runners 445" is spaced equally around the circumference of the through bore 430. The example controlling member 440 further includes a tab 460 spaced between an adjacent pair of runners (445a" and 445b"). Another example of the controlling member 440 includes a plurality of runners spaced unequally around the circumference of the through bore with a tab spaced between an adjacent pair of runners. In some examples, the tab 460 extends part of the length of the screw 400 and is different than a runner. While the one way or "keyed" feature of the screw 400 is described with reference to the example arrangements above, those skilled in the art will readily recognize that other arrangements are possible.

Other examples of the screw 400 include a depth stop, such as the open depth stop 25 described above with reference FIG. 5 and the closed depth stop 65 described above with reference FIG. 18. The depths stop engages a depth stop of the driver 450 such that a distal end of the driver extends beyond the distal end of the body. In still other examples of the screw 400, the proximal end 410 of the body 405 aligns with a hash mark on a distal end of the driver and a number associated with the hash mark identifies the length of the body 405 of the screw 400.

In an example procedure to install the screw 400 into bone 401, the surgeon may remove the driver 450 from the body 405 of the screw 400 that has been partly inserted into bone 401. The surgeon reinserts the driver 450 into the body 405 of the screw 400 and engages the controlling member 440. The surgeon confirms the orientation of the driver 450 based on the engagement of the controlling member 440 with the driver 450. Engaging the controlling member 440 tells the surgeon that the driver 450 is in the driving orientation. The lack of engagement tells the surgeon that the driver 450 is in an orientation different than the driving orientation. In the event the driver 450 does not engage the controlling member 440 (e.g., the surgeon turns driver 450 but the screw 400 does not turn), the surgeon rotates the driver 450 within the through bore 430 until the driver 450 engages the controlling member 440 (e.g., the surgeon turns driver and the screw turns).

In the example procedure, each time the surgeon removes and reinserts the driver 450 into the screw, the surgeon controls and confirms the orientation of the driver 450 using the controlling member 440. This is advantageous because the surgeon may have to remove and reinsert the driver 450 several times during the procedure in order to install the screw 400 into bone 401, completely.

Some examples of the screw 400 may be a part of an screwing system that includes the above-described driver 450. In an example system, the screw 400 maybe "preloaded" and disposed on at a distal end of the driver 450.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method comprising:
    removing a driver from a body of an interference screw inserted into bone, the body having a proximal end, a distal end, and a longitudinal axis extending between the proximal end and distal end, the body defining a through bore extending between the proximal end and distal end along the longitudinal axis, the through bore having a surface;
    engaging a controlling member formed by the surface of the through bore with the driver, the controlling member being engaged by the driver when the driver is in a driving orientation with respect to the controlling member and not being engaged by the driver when the driver is in an orientation different than the driving orientation;
    confirming the orientation of the driver in the body of the interference screw based on the engagement of the controlling member with the driver; and
    rotating the driver within the through bore with respect to the controlling member, about the longitudinal axis of the body, until the driver engages the controlling member.

2. The method of claim 1 further comprising inserting the driver into the through bore until a depth stop of the driver engages a depth stop extending, longitudinally, a partial length of the body such that a distal end of the driver extends beyond the distal end of the body.

3. The method of claim 1 wherein the controlling member includes a plurality of runners extending between the proximal end and distal end of the body along the longitudinal axis, the plurality of runners spaced equally around the circumference of the through bore, and one of the plurality of runners is of different shape and/or size than other runners.

4. The method of claim 1 wherein the controlling member includes a plurality of runners extending between the proximal end and distal end of the body along the longitudinal axis, the plurality of runners spaced unequally around the circumference of the through bore.

5. A method comprising:
   inserting, initially, a driver into a through bore defined by a body of an interference screw inserted into bone, the through bore extending between a proximal end and a distal end of the body along a longitudinal axis extending between the proximal end and distal end of the body, the through bore having a surface;
   rotating the driver within the through bore, about the longitudinal axis of the body, until the driver engages a controlling member formed by the surface of the through bore, the engagement confirming a driving orientation of the driver with respect to the controlling member; and
   driving the interference screw further into the bone with the driver in the driving orientation.

6. The method of claim 5 further comprising inserting the driver further into the through bore until a depth stop of the driver engages a depth stop extending, longitudinally, a partial length of the body such that a distal end of the driver extends beyond the distal end of the body.

7. The method of claim 5 wherein the controlling member includes a plurality of runners extending between the proximal end and distal end of the body along the longitudinal axis, the plurality of runners spaced equally around the circumference of the through bore, and one of the plurality of runners is of different shape and/or size than other runners.

8. The method of claim 5 wherein the controlling member includes a plurality of runners extending between the proximal end and distal end of the body along the longitudinal axis, the plurality of runners spaced unequally around the circumference of the through bore.

* * * * *